United States Patent [19]

Reiffenrath et al.

[11] Patent Number: 5,626,793

[45] Date of Patent: May 6, 1997

[54] LIQUID-CRYSTALLINE COMPOUNDS

[75] Inventors: Volker Reiffenrath, Rossdorf; Herbert Plach; Detlef Pauluth, both of Darmstadt; Reinhard Hittich, Modautal; Eike Poetsch, Mühltal; Thomas Geelhaar, Mainz; Georg Weber; Ekkehard Bartmann, both of Erzhausen, all of Germany

[73] Assignee: Merck Patent Gesellschaft mit beschrankter Haftung, Darmstadt, Germany

[21] Appl. No.: 464,938

[22] Filed: Jun. 5, 1995

Related U.S. Application Data

[63] Continuation of Ser. No. 844,676, Apr. 10, 1992.

[30] Foreign Application Priority Data

| Feb. 2, 1991 | [DE] | Germany | 41 04 126.7 |
| Mar. 26, 1991 | [DE] | Germany | 41 09 809.9 |
| Aug. 3, 1991 | [DE] | Germany | 41 25 844.4 |
| Aug. 20, 1991 | [DE] | Germany | 41 27 450.4 |

[51] Int. Cl.$^6$ .................... C09K 19/30; C09K 19/12
[52] U.S. Cl. .................... 252/299.63; 252/299.66; 570/129; 570/144
[58] Field of Search .................... 252/299.63, 299.66; 570/129, 144

[56] References Cited

U.S. PATENT DOCUMENTS

| 4,880,562 | 11/1989 | Kitano et al. | 252/299.63 |
| 4,886,619 | 12/1989 | Janulis et al. | 252/299.1 |
| 4,908,152 | 3/1990 | Goto et al. | 252/299.63 |
| 5,053,162 | 10/1991 | Kitano et al. | 252/299.61 |
| 5,082,587 | 1/1992 | Janulis | 252/299.01 |
| 5,122,297 | 6/1992 | Reiffenrath et al. | 252/299.63 |
| 5,190,688 | 3/1993 | Sage et al. | 252/299.01 |
| 5,196,140 | 3/1993 | Poetsch et al. | 252/299.6 |
| 5,198,151 | 3/1993 | Kuratate et al. | 252/299.61 |
| 5,262,082 | 11/1993 | Janulis et al. | 252/299.01 |
| 5,308,541 | 5/1994 | Hittich et al. | 252/299.63 |

*Primary Examiner*—Philip Tucker
*Attorney, Agent, or Firm*—Millen, White, Zelano, & Branigan, P.C.

[57] ABSTRACT

A nematic liquid crystalline medium having at least two liquid crystalline components with at least one being of formula I $$R-(A_1-Z_1)_m-\phantom{X}-Z(A)_o-O-CH_2CF_3 \quad \text{I}$$

(with F substituents on the phenylene ring)

wherein

R is H, a straight-chain alkyl or alkenyl radical having 1 to 15 carbon atoms, it also being possible to replace one or more $CH_2$ groups in these radicals, independently of one another, by —O—, —S—, (diamond shape), —CO—, —CO—O—, —O—CO— or —O—CO—O— in such a way that oxygen atoms are not linked directly to one another, $Z_1$ and Z are each, independently of one another, —$CH_2$—$CH_2$—, —CH=CH—, —C≡C— or a single bond, and one of the radicals $Z^1$ and Z is alternatively —$(CH_2)_4$— or —CH=CH—$CH_2CH_2$—, A and $A^1$ are each, independently of one another, trans-1, 4-cyclohexylene in which, in addition, one or two nonadjacent $CH_2$ groups may be replaced by —O—, or are 1,4-phenylene which is unsubstituted or monosubstituted or disubstituted by fluorine and/or Cl atoms and in which, in addition, one or two CH groups may be replaced by N, m is 0, 1, 2 or 3, o and s are 0, 1 or 2, where (s+o) is >2.

These liquid crystalline media find use in electro-optical display elements.

9 Claims, No Drawings

LIQUID-CRYSTALLINE COMPOUNDS

This is a continuation, of the application Ser. No. 08/844,676 filed Apr. 10, 1992 now pending.

The invention relates to liquid-crystalline compounds of the formula I

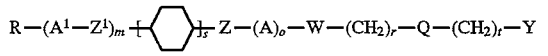

in which

R is H, an alkyl or alkylene [sic] radical having 1 to 15 carbon atoms which is unsubstituted, monosubstituted by CN or $CF_3$ or at least monosubstituted by halogen, it also being possible for one or more $CH_2$ groups in these radicals each to be replaced, independently of one another, by —O—, —S—,

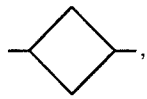

—CO—, —CO—O—, —O—CO— or —O—CO—O— in such a way that oxygen atoms are not linked directly to one another, $Z^1$ and Z are each, independently of one another, —$CH_2CH_2$—, —CH=CH—, —C≡C— or a single bond, and one of the radicals $Z^1$ and Z is alternatively —$(CH_2)_4$— or —CH=CH—$CH_2CH_2$—, A and $A^1$ are each, independently of one another, trans-1,4-cyclohexylene in which, in addition, one or two non-adjacent $CH_2$ groups may be replaced by —O—, or are 1,4-phenylene which is unsubstituted or monosubstituted or disubstituted by fluorine and/or Cl atoms and in which, in addition, one or two CH groups may be replaced by N, m is 0, 1, 2 or 3, o+s [sic] is 0, 1 or 2, where (s+o) is ≧2, W is —O—, —COO— or a single bond, Q is —O—, —CH=CH— or a single bond, r is 1 to 7, t is 0 to 7, and Y is F, Cl, $CF_3$, $OCF_3$, $CHF_2$, $OCHF_2$ or $OCH_2F$.

The invention furthermore relates to the use of these compounds as components of liquid-crystalline media, and to liquid-crystal and electro-optical display elements which contain the liquid-crystalline media according to the invention.

The compounds of the formula I can be used as components of liquid-crystalline media, in particular for displays based on the principle of the twisted cell, the guest-host effect, the effect of deformation of aligned phases or the effect of dynamic scattering.

The substances employed hitherto for this purpose have certain disadvantages, for example excessively high melting points, excessively low clearing points, in adequate stability towards the action of heat, light or electric fields, inadequate electrical resistance, excessively high temperature dependence of the threshold voltage, or unfavorable elastic and/or dielectric properties.

In particular in displays of the supertwist type (STN) having twist angles of significantly greater than 220° or in displays having an active matrix, the materials employed hitherto have disadvantages.

The invention had the object of finding novel stable liquid-crystalline or mesogenic compounds which are suitable as components of liquid-crystalline media and at the same time, have, in particular, relatively low viscosity and relatively high dielectric anisotropy and high nematogeneity.

It has been found that compounds of the formula I are eminently suitable as components of liquid-crystalline media. In particular, they have relatively low viscosities and high nematogeneities. They can be used to obtain stable liquid-crystalline media having a broad mesophase range and advantageous values for the optical and dielectric anisotropy. These media furthermore have very good low-temperature behavior, ie. excellent solubility in the conventional LC materials, at the same time occurrence of smectic phases being effectively suppressed.

Liquid crystals of the formula

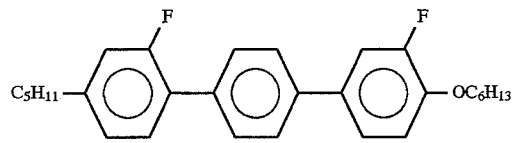

have already been disclosed in WO 8902425. JP 59/155485-A2 mentions a compound of the formula

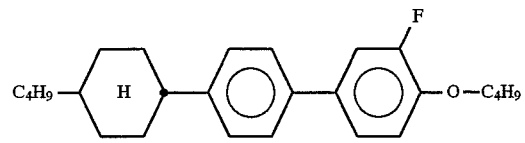

Finally, EP 278665 describes compounds of the formula

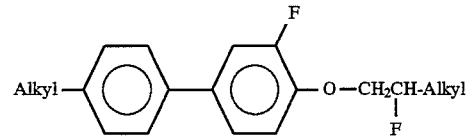

DE 31 36 624, DE 32 09 178 and DE 34 10 734 disclose compounds of the following formulae:

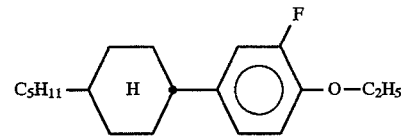

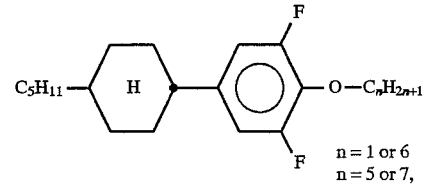

n = 1 or 6
n = 5 or 7,
m = 1, 2, 6, 10 or 11.

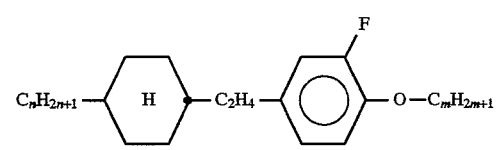

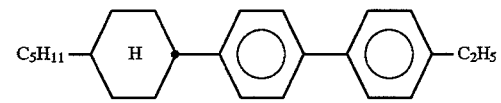

J [sic] 59/01.684 discloses 3-fluoro-4-substituted 4-bicyclohexylbenzenes of the formula

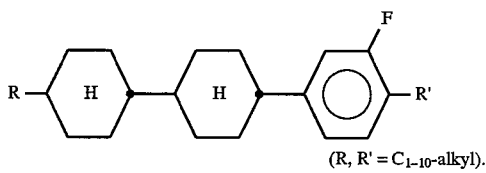

(R, R' = C$_{1-10}$-alkyl).

WO 88/05 803 A relates to esters of the general formula

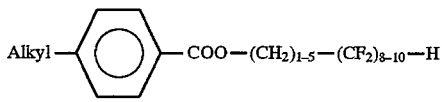

EP 0 360 521 A describes compounds of the general formula.

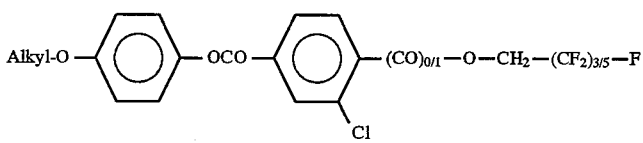

WO 89/02 884 discloses trifluoromethyl ethers of the formula

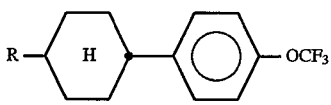

Finally, DE-A 39 09 802 describes compounds of the formula

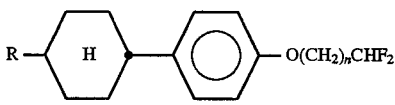

EP-A 0 168 683 discloses liquid crystals of the following formulae:

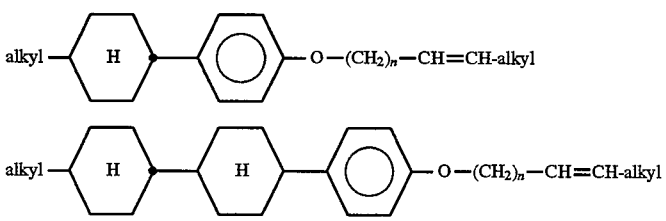

The compounds of the formula I where Y=CF$_3$ facilitate both STN displays having a very steep electro-optical characteristic line and displays having an active matrix and excellent long-term stability. Compared with non-fluorinated compounds, the compounds according to the invention have both higher Δε and higher ε$_⊥$. Due to their particularly favorable elastic properties, they are particularly suitable as components for TFT mixtures. A suitable choice of r and s allows the threshold voltages to be significantly reduced in displays of both types.

However, in view of the very wide variety of areas of application of such compounds, it was desirable to have available further compounds which have properties precisely customized to the particular applications.

In addition, the provision of compounds of the formula I very generally considerably broadens the range of liquid-crystalline substances which are suitable, from various applicational points of view, for the preparation of liquid-crystalline mixtures.

The compounds of the formula I have a broad range of applications. Depending on the choice of substituents, these compounds can be used as base materials from which liquid-crystalline media are predominantly composed; however, it is also possible to add compounds of the formula I to liquid-crystalline base materials from other classes of compound, in order, for example, to influence the dielectric and/or optical anisotropy of a dielectric of this type and/or to optimize its threshold voltage and/or its viscosity.

In the pure state, the compounds of the formula I are colorless and form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media containing at least one compound of the formula I and to liquid-crystal display elements, in particular electro-optical display elements, which contain media of this type.

Above and below, R, A$^1$, A, Z$^1$, Z, W, Q, Y, m, o, s, r and t are as defined above, unless expressly stated otherwise. If A$^1$ and A are a substituted 1,4-phenylene ring, the phenylene ring is preferably substituted in the 2-, 2,3- or 2,6-position by fluorine.

Z$^1$ and Z are preferably a single bond or —CH$_2$CH$_2$—.

If one of the radicals Z$^1$ and Z is —(CH$_2$)$_2$—, —(CH$_2$)$_4$— or —CH=CH—CH$_2$CH$_2$—, the other radical Z$^1$ or Z is preferably a single bond.

Preferred compounds of this type conform to the sub-formula I'

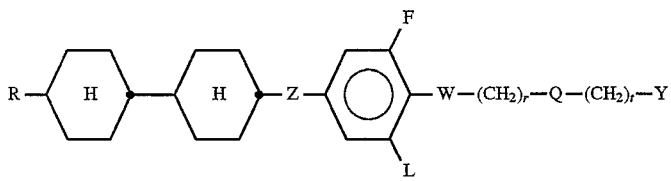

in which Z is —(CH$_2$)$_4$— or —CH=CH—CH$_2$CH$^2$—, and R, r, t, L, W, Q and Y are as defined in formula I.

Preference is likewise given to compounds of the sub-formula I"

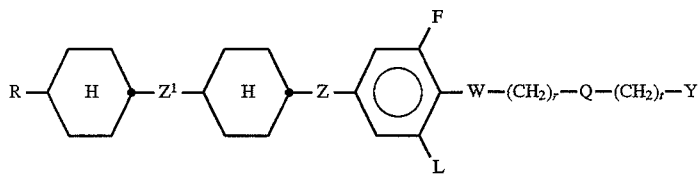

in which L is H or F, and R, Z$^1$, W, Q, Y, r and t are as defined in claim 1. If t=0, Q is preferably a single bond.

Y may also be H if W=0 or denote [sic] a single bond.

In the following, for reasons of simplicity, A" is a 1,4-cyclo-hexylene radical, B is a radical of the formula

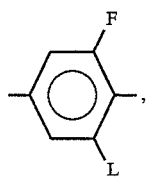

where L is preferably F, Y is preferably F, Cl or CF$_3$, and r and s are preferably 1, 2, 3 or 4. Q is preferably a single bond.

The compounds of the formula I accordingly include compounds of the sub-formulae

| | |
|---|---|
| R-A"-A"-B—W—(CH$_2$)$_r$—(CH$_2$)$_t$—Y | I"a |
| R-A"-A"-B—W—(CH$_2$)$_r$—O—(CH$_2$)$_t$—Y | I"b |
| R-A"-Z$^1$-A"-B—W—(CH$_2$)$_r$—(CH$_2$)$_t$—Y | I"c |
| R-A"-Z$^1$-A"-B—W(CH$_2$)$_r$—O—(CH$_2$)$_t$—Y | I"d |
| R-A"-A"-Z$^2$-B—W—(CH$_2$)$_r$—(CH$_2$)$_t$—Y | I"e |
| R-A"-A"-Z$^2$-B—W—(CH$_2$)$_r$—O—(CH$_2$)$_t$—Y | I"f |
| R-A"-Z$^1$-A"-Z$^2$-B—W—(CH$_2$)$_r$—(CH$_2$)$_t$—Y | I"g |
| R-A"-Z$^1$-A"-Z$^2$-B—W—(CH$_2$)$_r$—O—(CH$_2$)$_t$—Y | I"h |

Of these, particular preference is given to those of the sub-formulae I"a, I"b, I"e and I"f. In the compounds of the sub-formulae I"c to I"h, Z$^1$ and Z are —CH$_2$CH$_2$—, —CH=CH— or —C≡C—, preferably —CH$_2$CH$_2$—.

Particular preference is also given to the compounds of the formula IA,

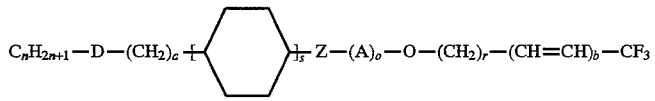

in which n is 0 to 7, D is —O—, —CH=CH— or a single bond, a is 1 to 5, b is 0 or 1, and Z, A, o, s and r are as defined in claim 1.

Particularly preferred sub-formulae of compounds IA are the compounds of the formula Ia

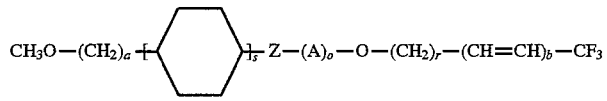

in which a is 1 to 5, b is 0 or 1, s is 1 or 2 and A, Z, o and r are as defined in claim 1;

the compounds of the formula Ib

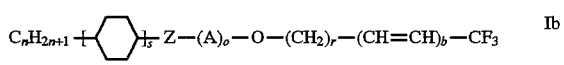

in which n is 1 to 7, s is 1 or 2, b is 0 or 1 and A, Z, o and r are as defined in claim 1;

the compounds of the formula Ic,

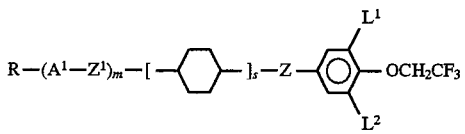

in which $L^1$ is H, F or Cl, $L^2$ is F or Cl, and R, $A^1$, $Z^1$, Z m and s are as defined in claim 1.

If R in the formula I is an alkyl radical and/or an alkoxy radical, this may be straight-chain or branched. It is preferably straight-chain, has 2, 3, 4, 5, 6 or 7 carbon atoms and is accordingly preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R is an alkenyl radical, it may be straight-chain or branched. It is preferably straight-chain and has 2 to 10 carbon atoms. Accordingly, it is in particular vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7-or non-8-enyl, or dec-1-, 2-, 3-, 4-, 5-, 6-, 7-, 8-or dec-9-enyl.

If R is an alkyl radical in which one $CH_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 carbon atoms.

Accordingly, they are in particular acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R is an alkenyl radical in which one $CH_2$ group adjacent to the vinyl group has been replaced by CO or CO—O or O—CO—, this may be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxy-butyl, 5-methacryloyloxypentyl, 6-methacryloyloxyhexyl, 7-methacryloyloxyheptyl, 8-methacryloyloxyoctyl or 9-methacryloyloxynonyl.

If R is an alkyl or alkenyl radical which is monosubstituted by CN or $CF_3$, this radical is preferably straight-chain and the substitution by CN or $CF_3$ is in the ω-position.

If R is an alkyl or alkenyl radical which is at least monosubstituted by halogen, this radical is preferably straight-chain and halogen is preferably F or Cl. In the case of multiple substitution, halogen is preferably F. The resultant radicals also include perfluorinated radicals. In the case of monosubstitution, the fluorine or chlorine substituent may be in any desired position, but is preferably in the ω-position.

Compounds of the formula I which contain wing groups R which are suitable for polymerization reactions are suitable for the formation of liquid-crystalline polymers.

Compounds of the formula I containing branched wing groups R may occasionally be of importance due to better solubility in the customary liquid-crystalline base materials, but in particular as chiral dopants if they are optically active. Smectic compounds of this type are suitable as components of ferroelectric materials. Compounds of the formula I having $S_A$ phases are suitable, for example, for thermally addressed displays.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

If R is an alkyl radical in which two or more $CH_2$ groups have been replaced by —O—and/or —CO—O—, this may be straight-chain or branched. It is preferably branched and has 3 to 12 carbon atoms. Accordingly, it is in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl) butyl, 5,5-bis(methoxycarbonyl)pentyl, 6,6-bis (methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl) propyl, 4,4-bis(ethoxycarbonyl)butyl or 5,5-bis (ethoxycarbonyl)hexyl.

Of these compounds of the formula I and the subformulae, those are preferred in which at least one of the radicals present therein has one of the preferred meanings indicated.

Some very particularly preferred smaller groups of compounds are those of the sub-formulae I1 to I48, in which L is H or F, N=1–14 and r and t are each 1–7.

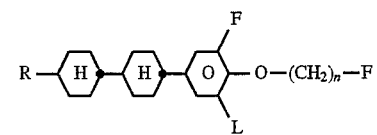 I1
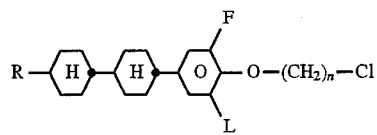 I2
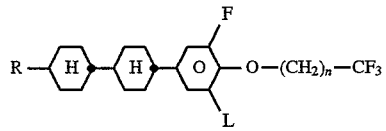 I3
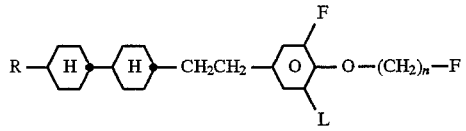 I4
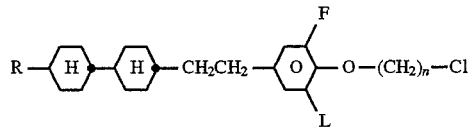 I5
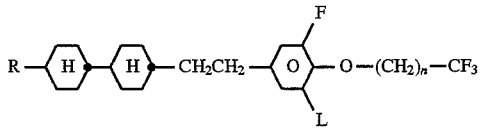 I6
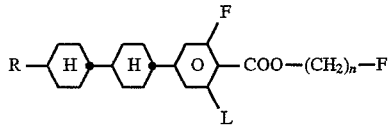 I7
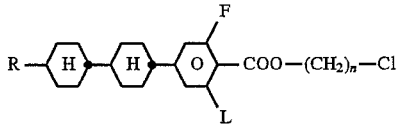 I8
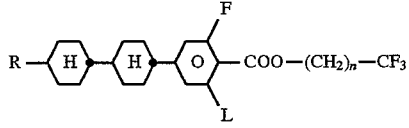 I9
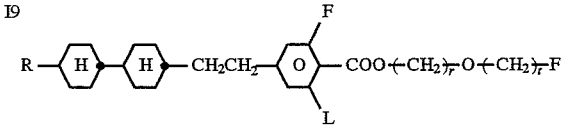 I10
I11
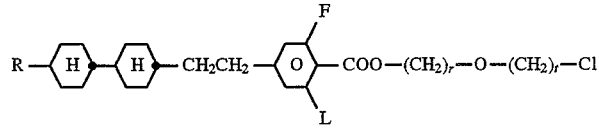
I12
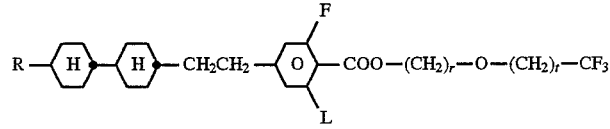
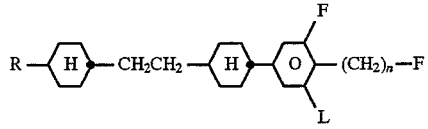 I13
I14
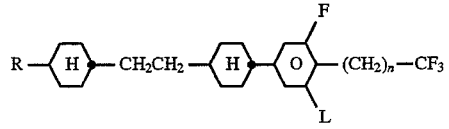 I15
I16
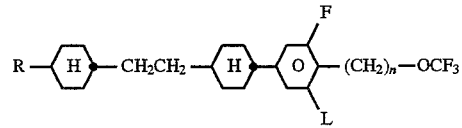 I17
I18
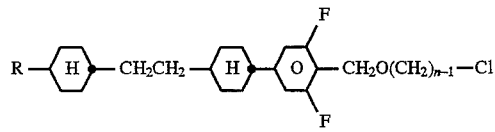 I19
I20
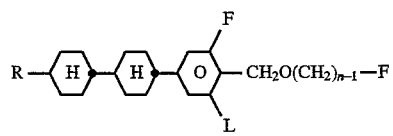 I21
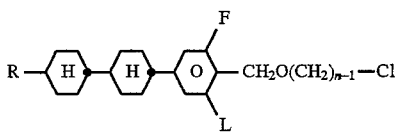 I22

-continued

R–[H]–[H]–[O(F,L)]–CH₂O(CH₂)ₙ₋₁–CF₃  I23
R–[H]–[H]–O–(CH₂)ᵣ–CF₃  I24
R–[H]–[H]–O–(CH₂)ᵣ–CH=CH–CF₃  I25
R–[H]–[O]–O–(CH₂)ᵣ–CF₃  I26
R–[H]–[O(F,L)]–(CH₂)ᵣ–CF₃  I27
R–[O]–[O]–(CH₂)ᵣ–CF₃  I28
R–[O]–[O(F,L)]–(CH₂)ᵣ–CF₃  I29
R–[H]–[O]–[O]–(CH₂)ᵣ–CF₃  I30
R–[H]–[O]–[O(F,L)]–(CH₂)ᵣ–CF₃  I31
R–[H]–[H]–[O]–(CH₂)ᵣ–CF₃  I32
R–[H]–[H]–CH₂CH₂–[O]–(CH₂)ᵣ–CF₃  I33
R–[H]–(CH₂)₄–[O]–(CH₂)ᵣ–CF₃  I34
R–[H]–(CH₂)₄–[O(F,F)]–(CH₂)ᵣ–CF₃  I35
R–[H]–[O]–O–(CH₂)ᵣ–CH=CH–CF₃  I36
R–[H]–[O(F,L)]–(CH₂)ᵣ–CH=CH–CF₃  I37
R–[O]–[O]–(CH₂)ᵣ–CH=CH–CF₃  I38
R–[O]–[O(F,L)]–(CH₂)ᵣ–CH=CH–CF₃  I39
R–[H]–[O]–[O]–(CH₂)ᵣ–CH=CH–CF₃  I40
R–[H]–[O]–[O(F,L)]–(CH₂)ᵣ–CH=CH–CF₃  I41
R–[H]–[H]–[O]–(CH₂)ᵣ–CH=CH–CF₃  I42
R–[H]–[H]–[O(F,L)]–(CH₂)ᵣ–CH=CH–CF₃  I43
R–[H]–[H]–CH₂CH₂–[O]–(CH₂)ᵣ–CH=CH–CF₃  I44
R–[H]–[H]–CH₂CH₂–[O(F,L)]–(CH₂)ᵣ–CH=CH–CF₃  I45
R–[H]–(CH₂)₄–[O]–(CH₂)ᵣ–CH=CH–CF₃  I46

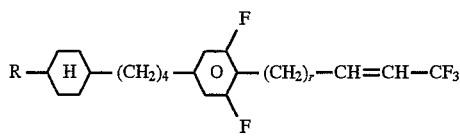

147

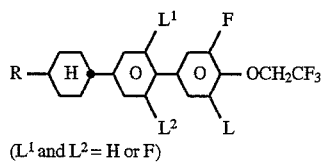

148

(L¹ and L² = H or F)

The compounds of the formula I are prepared by methods known per se, as described in the literature (for example in the standard works such as Houben-Weyl, Methoden der Organischen Chemie, Georg-Thieme-Verlag, Stuttgart, Vol. IX, pp. 867 ff), to be precise under reaction conditions which are known and suitable for the said reactions. Use may also be made here of variants which are known per se, but are not described here in greater detail.

The compounds of the formula I according to the invention where W=—O— and

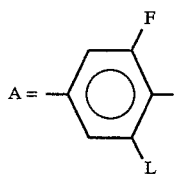

can be prepared, for example, by metalating a compound of the formula II

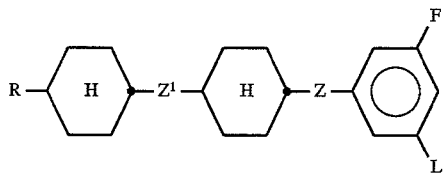

in which L is H or F, and R, Z¹ and Z are as defined above, in accordance with the reaction scheme below, and subsequently reacting the product with a suitable electrophile:

Scheme 1

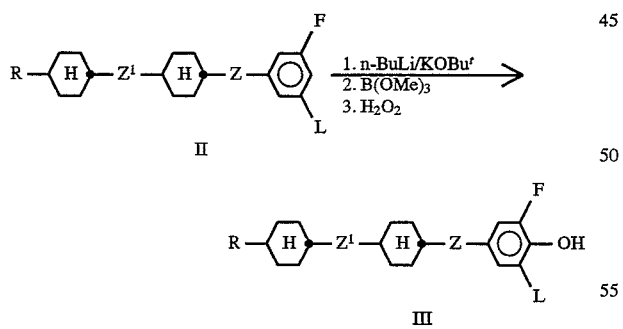

The compounds of the formula II where L=F are novel and are thus also the subject-matter of the invention. Furthermore, compounds of the formula II where L=F are a subject-matter of the invention.

The invention furthermore relates to liquid-crystalline media containing at least one compound of the formula II.

The compounds of the formula I (W=—O—) [sic] (W=—O— and

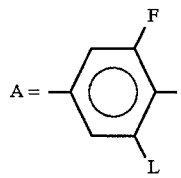

can be obtained from the resultant phenol of the formula III by known etherification methods, for example by reaction with Hal-(CH₂)ᵣ-Q-(CH₂)ₜ—Y (Hal=I, Br or Cl) in acetone/K₂CO₃, optionally in the presence of catalytic amounts of KI.

Further synthesis methods for the phenyl ethers, according to the invention are obvious to a person skilled in the art. For example, appropriately 5-substituted 1,3-difluorobenzene compounds or mono-fluorinated analogs (L=H) can be converted to the 2-O—(CH₂)ᵣ-Q-(CH₂)ₜ—Y-1,3-difluoro compounds or mono-fluorinated analogs (l=H) in accordance with the above scheme, and the radical

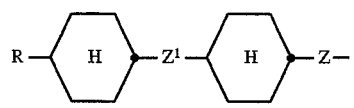

can subsequently be introduced by reactions which are customary in liquid-crystalline chemistry (for example etherification or coupling, for example as described in the article E. Poetsch, Kontakte (Darmstadt) 1988 (2), p. 15).

The compounds of the formula II can be prepared for example, by the following synthesis:

Scheme 2

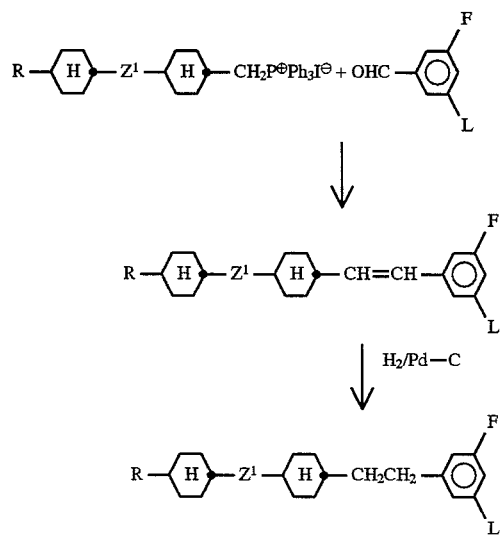

The synthesis of some particularly preferred compounds is indicated in greater detail below:

Scheme 3
(L = H or F)

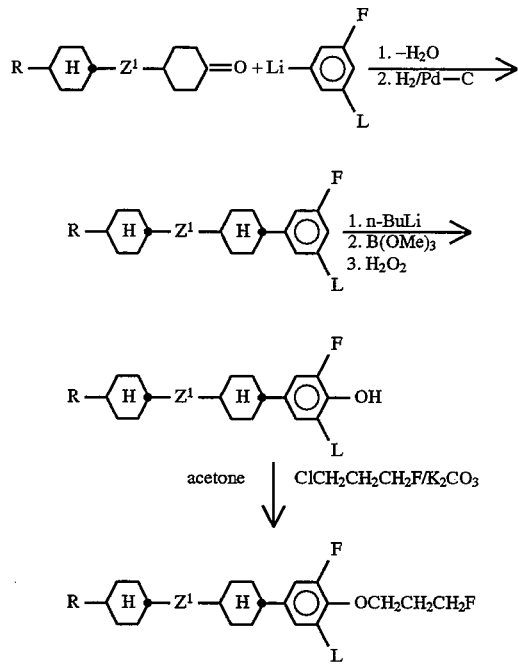

Scheme 4

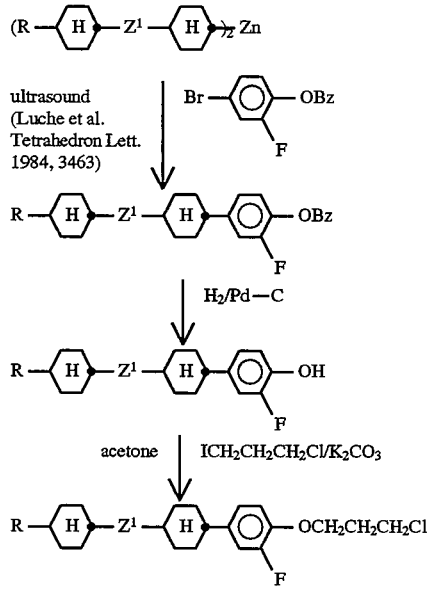

Scheme 5

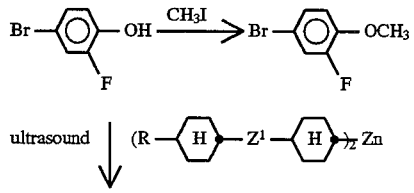

-continued
Scheme 5

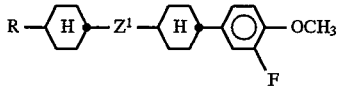

Phenyl ethers of the formula I are obtainable by etherification of corresponding hydroxyl compounds, preferably corresponding phenols, the hydroxyl compound expediently first being converted to a corresponding metal derivative, for example to the corresponding alkali metal alkoxide or alkali metal phenoxide by treatment with NaH, NaNH$_2$, NaOH, KOH, Na$_2$CO$_3$ or K$_2$CO$_3$. This can then be reacted with the appropriate alkyl halide, alkyl sulfonate or dialkyl sulfate, expediently in an inert solvent, such as, for example, acetone, 1,2-dimethoxyethane, DMF or dimethyl sulfoxide, or alternatively with an excess of aqueous or aquueous-alcoholicNaOH or KOH at temperatures between about 20° and 100° C.

Furthermore, the alkyl ethers may also be prepared by the method of Mitsunobu from the corresponding phenols and a hydroxyl compound in the presence of triphenylphosphine and diethyl azodicarboxylate (S. Bittner, Y. Assaf, Chemistry and Industry, 281 (1975); M. S. Manhas, W. H. Hoffman, B. Lal, A. K. Bose, J. Chem. Soc. Perkin I, 461 (1975):

Scheme 6

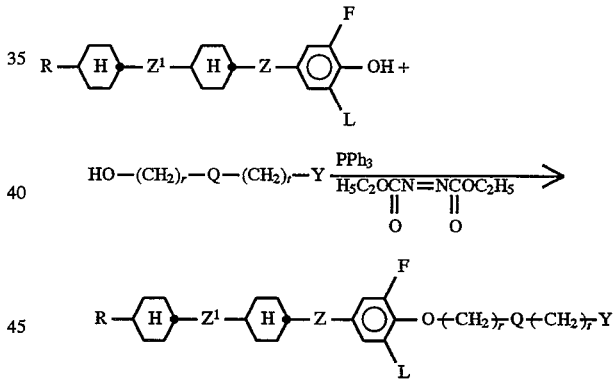

The starting materials for the preparation processes are either known or can be prepared analogously to known compounds.

The compounds of the formula I''' where Z=—(CH$_2$)$_4$— can be prepared in accordance with the following scheme (n=1–8):

Scheme 7
(L = H or F)

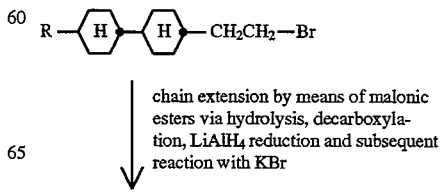

chain extension by means of malonic esters via hydrolysis, decarboxylation, LiAlH$_4$ reduction and subsequent reaction with KBr

17

-continued
Scheme 7
(L = H or F)

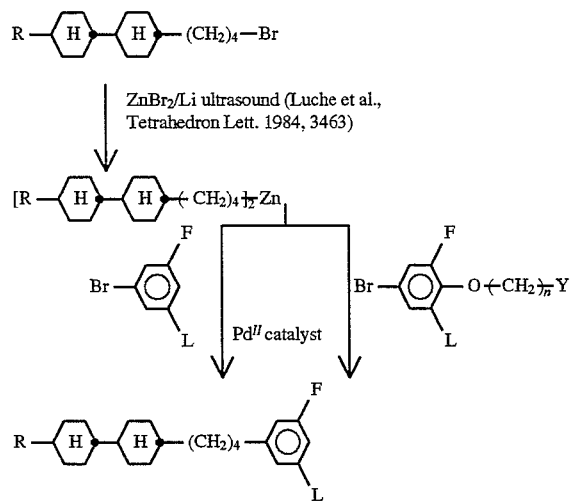

In the Pd(II)-catalysed coupling reaction, the target product I''' is either formed directly or a precursor is formed into which the radical —O—$(CH_2)_r$-Q-$(CH_2)_s$—Y is introduced entirely analogously to the abovementioned methods for compounds of the formula I.

The phenyl esters of the formula I according to the invention (Q=—COO—) are obtained from the compounds of the formula II in accordance with the following reaction scheme:

Scheme 8
(L = H or F)

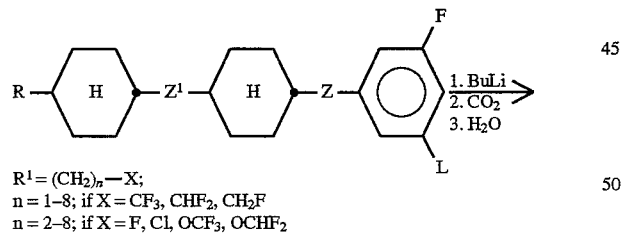

$R^1 = (CH_2)_n$—X;
n = 1–8; if X = $CF_3$, $CHF_2$, $CH_2F$
n = 2–8; if X = F, Cl, $OCF_3$, $OCHF_2$

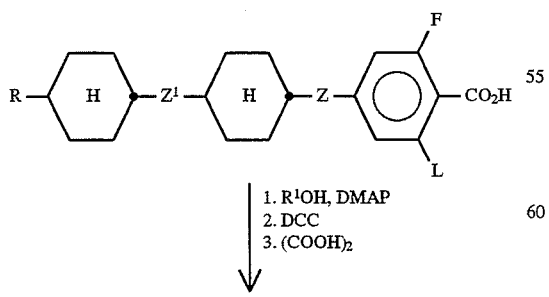

1. $R^1OH$, DMAP
2. DCC
3. $(COOH)_2$

18

-continued
Scheme 8
(L = H or F)

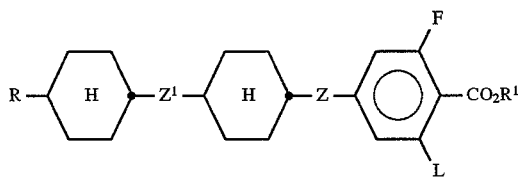

The benzene derivatives of the formula I according to the invention, in which Q is a single bond, are obtained in accordance with the following schemes:

Scheme 9
(L = H or F)

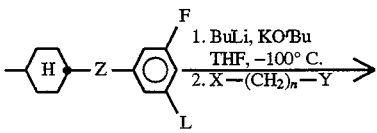

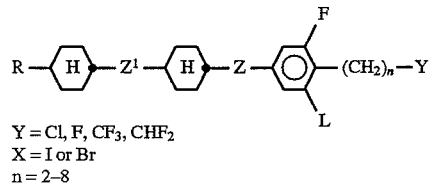

Y = Cl, F, $CF_3$, $CHF_2$
X = I or Br
n = 2–8

Scheme 10 (L = H or F)

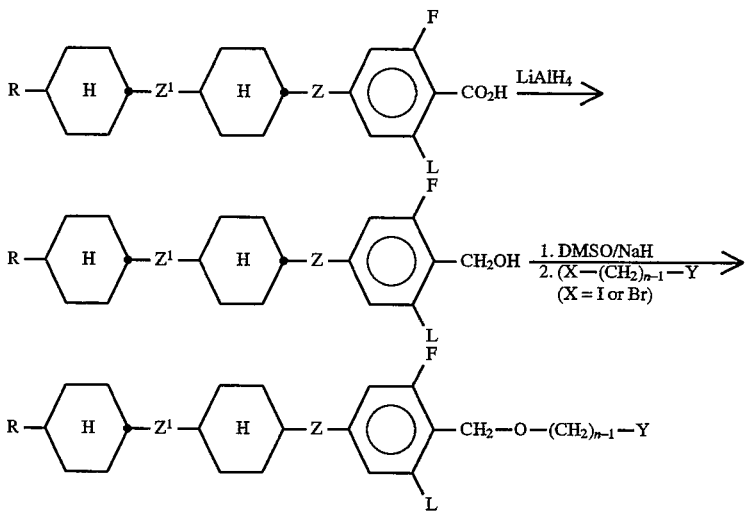

The trifluoroalkyl and -alkenyl ethers of the formula

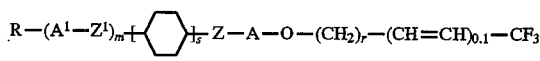

can be obtained by known etherification methods, for example by reacting 4-substituted phenols with Hal-$(CH_r)$ $_2$—$(CH=CH)_{0,1}$—$CF_3$, where Hal is I, Br or Cl, in acetone and potassium carbonate, optionally in the presence of catalytic amounts of potassium iodide.

The etherification is advantageously carried out in the presence of an inert solvent. Highly suitable solvents are, in particular, ethers, such as diethyl ether, di-n-butyl ether, THF, dioxane or anisole, ketones, such as acetone, butanone or cyclohexanone, hydrocarbons, such as benzene, toluene or xylene, or halogenated hydrocarbons, such as tetrachloromethane, dichloromethane or tetrachloroethylene.

The synthesis of the trifluoroalkyl and -alkenyl compounds according to the invention is shown in the following schemes:

Scheme 11

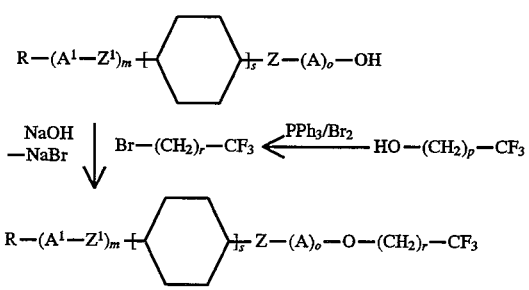

Scheme 12

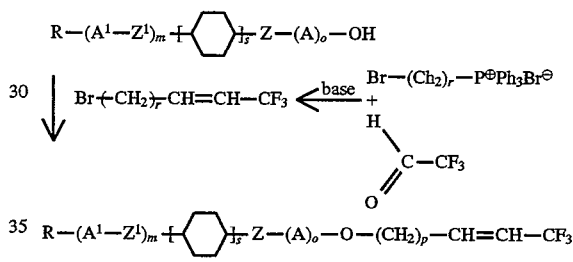

Scheme 13

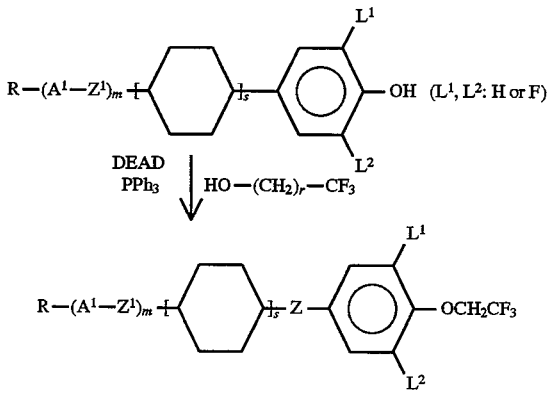

The compounds of the formula

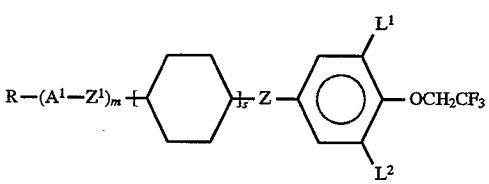

can be prepared as follows:

Scheme 14
(L = H or F)

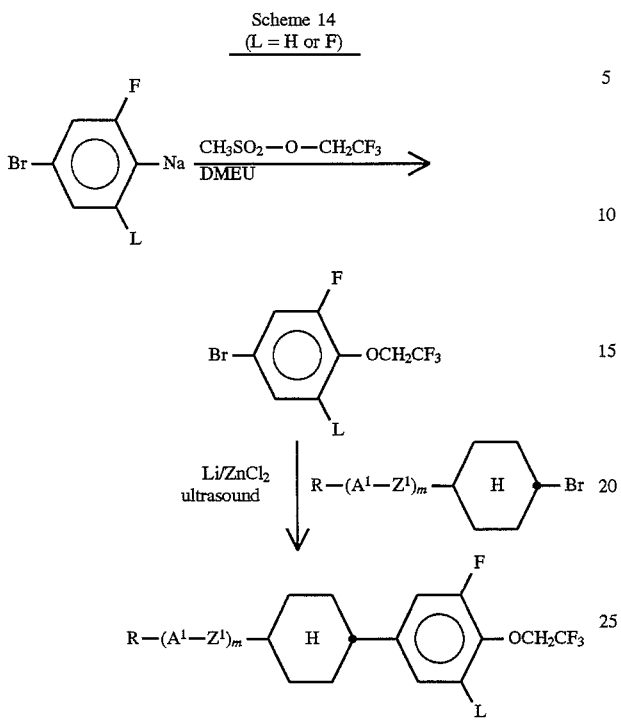

or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes optionally halogenated stilbenes, benzyl phenyl ethers, tolanes and substituted cinnamic acids. The 1,4-phenylene groups in these compounds may also be fluorinated.

The most important compounds suitable as further constituents of media according to the invention can be characterized by the formulae 1, 2, 3, 4 and 5:

| | |
|---|---|
| R'-L-E-R" | 1 |
| R'-L-COO-E—R" | 2 |
| R'-L-OOC-E—R" | 3 |
| R'-L-CH₂CH₂-E-R" | 4 |
| R'-L-C≡C—E-R" | 5 |

In the formulae 1, 2, 3, 4 and 5, L and E, which may be identical or different, are in each case, independently of one another, a divalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Bio [sic] is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

Scheme 15

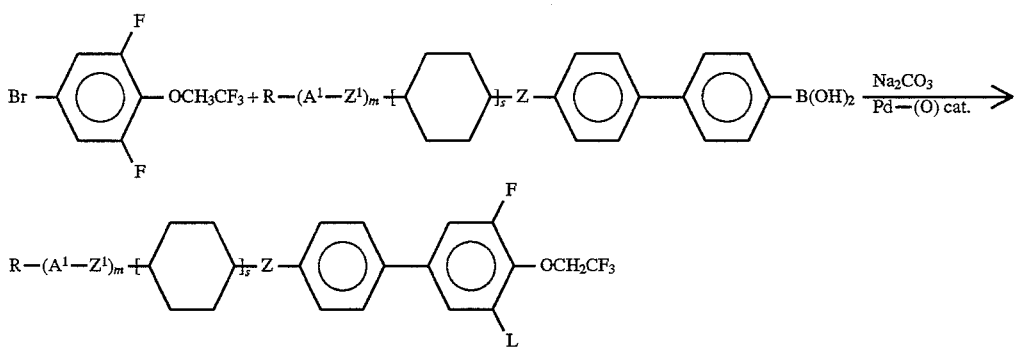

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- One of the radical [sic] L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group comprising -Phe-Cyc-, -Cyc-Cyc-, -G-Phe- and -G-Cyc-.

In a smaller sub-group of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are labeled with the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5 which is known as group B, R" is —F, —Cl, —NCS or —(O)$_i$CH$_{3-(k+1)}$F$_k$Cl$_1$, where i is 0 or 1, and k+l is 1, 2 or 3; the compounds in which R" has this meaning are labeled with the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is known as group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably contain one or more compounds selected from group A and/or group B and/or group C. The proportions by weight of the compounds from these groups in the media according to the invention are preferably Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular media according to the invention preferably being 5 to 90% and in particular 10 to 90%.

The media according to the invention preferably contain 1 to 40%, particularly preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

The examples below are intended to illustrate the invention without representing a limitation. "Customary work-up" means that water is added, the mixture is extracted with methylene chloride, the organic phase is separated off, dried and evaporated, and the product is purified by crystallization and/or chromatography. Above and below, percent data are percent by weight. All temperatures are given in degrees Celsius. m.p. is melting point and c.p.=clearing point. Furthermore, C=crystalline state, N=nematic phase, S=smectic phase and I=isotropic phase. The data between these symbols indicate the transition temperatures. Δn is optical anisotropy (589 nm, 20° C.). The viscosity (mm$^2$/sec) was determined at 20° C.

The following abbreviations are used:

| | |
|---|---|
| BuLi | butyllithium |
| DAST | diethylaminosulfur trifluoride |
| DCC | dicyclohexylcarbodiimide |
| DIBALH | diisobutylaluminum hydride |
| DMAP | 2-dimethylaminopyridine |
| DDQ | dichloride[sic]dicyanobenzoquinone |
| POT | potassium tertiary butoxide |
| NH$_4$Cl | ammonium chloride |
| THF | tetrahydrofuran |
| TMEDA | tetramethylethylenediamine |
| pTSOH | p-toluenesulfonic acid |

EXAMPLE 1

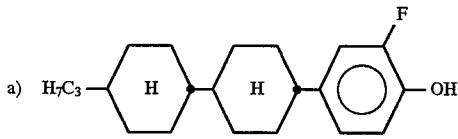

26 mmol of n-BuLi are added dropwise at −100° C. to a mixture comprising 26 mmol of 1-trans-4-(trans-4-n-propylcyclohexyl)-cyclohexyl-3-fluorobenzene (prepared as described in scheme 1), 4.1 g of potassium tert.-butoxide and 60 ml of THF. After the mixture has been stirred at −100° C. for one hour, 36 mmol of trimethyl borate are added dropwise at from −85° to −90° C. The mixture is stirred for a further 0.5 hour, and 42 mmol of acetic acid are then added dropwise at −20° C. The mixture is subsequently warmed to 30° C., and 4.2 ml of H$_2$O$_2$ are added dropwise at this temperature, and the mixture is stirred at from 50° to 60° C. for 2 hours. The mixture is allowed to cool to room temperature, and a 5% sodium dithione [sic] solution is added. Phase separation and conventional work-up give the phenol.

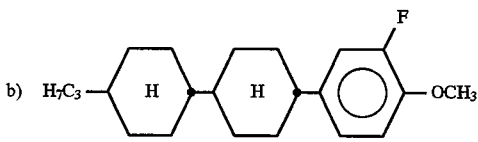

The phenol obtained is reacted with methyl iodide in acetone under reflux in the presence of potassium carbonate to give the methyl ether. Conventional work-up and chromatography on silica gel using hexane give the ether in pure form.

The following ethers of the formula

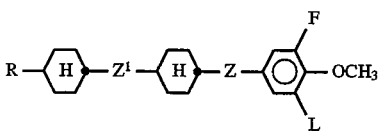

are prepared analogously.

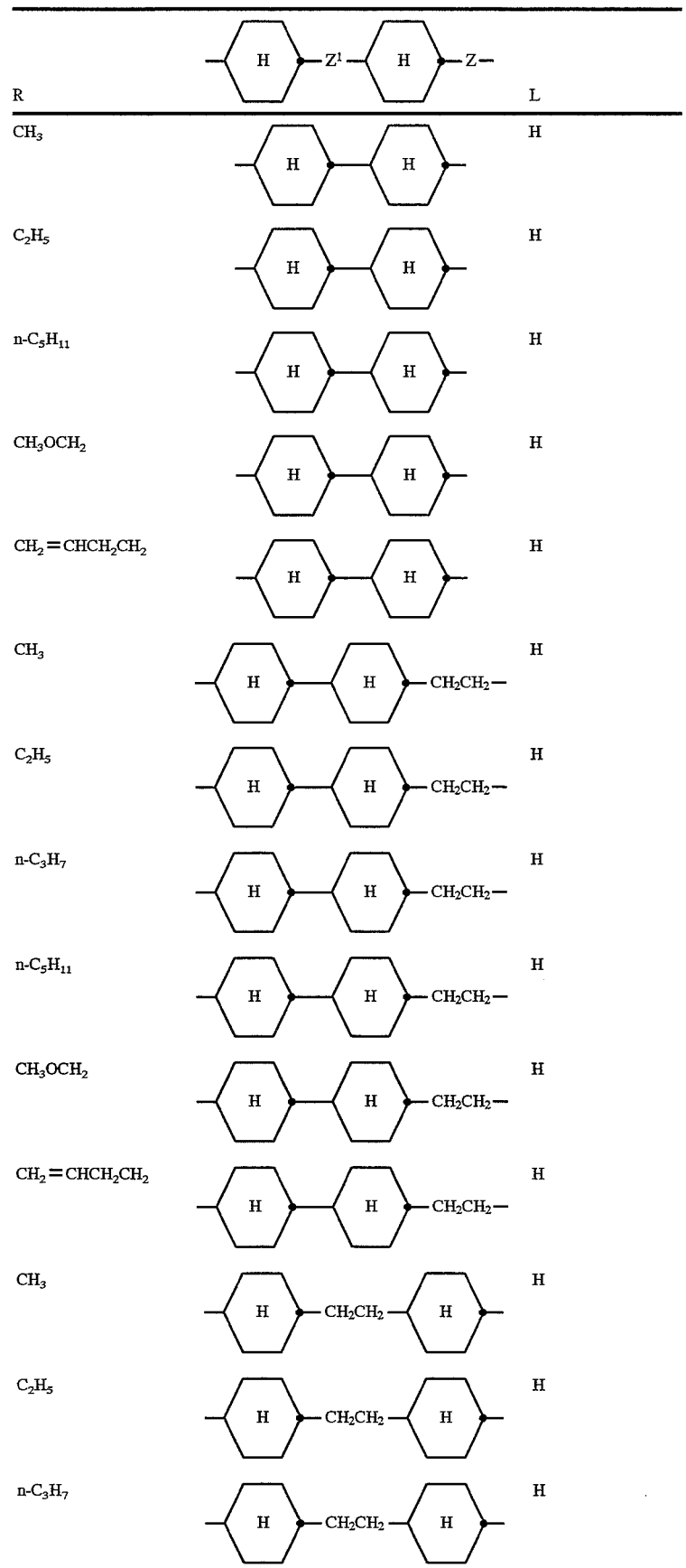

| R | H—Z¹—H—Z— | L |
|---|---|---|
| n-C₅H₁₁ | H—CH₂CH₂—H | H |
| CH₃OCH₂ | H—CH₂CH₂—H | H |
| CH₂=CHCH₂CH₂ | H—CH₂CH₂—H | N |
| n-C₅H₁₁ | H—H | F C 43 N 154.3 I |
| CH₃ | H—(CH₂)₄—H | |
| C₂H₅ | H—(CH₂)₄—H | |
| n-C₃H₇ | H—(CH₂)₄—H | |
| n-C₅H₁₁ | H—(CH₂)₄—H | |
| CH₃OCH₂ | H—(CH₂)₄—H | |
| CH₂=CHCH₂CH₂ | H—(CH₂)₄—H | |

Example 2 a) 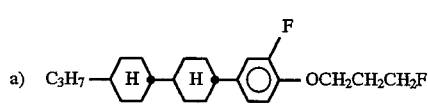

The fluorophenol prepared in Example 1a) is reacted with 1-chloro-3-fluoropropane in boiling acetone in the presence of potassium carbonate and a catalytic amount of potassium iodide to give the phenol ether. Conventional work-up and chromatography on silica gel using hexane gives the ether in pure form.

b) 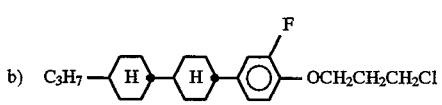

The fluorophenol prepared in Example 1a) is converted to the phenol ether using 1-chloro-3-iodopropane analogously to Example 2a).

The following compounds of the formula

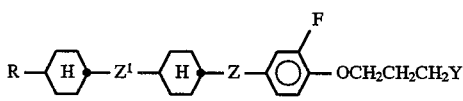

according to the invention are obtained analogously from the corresponding precursors:
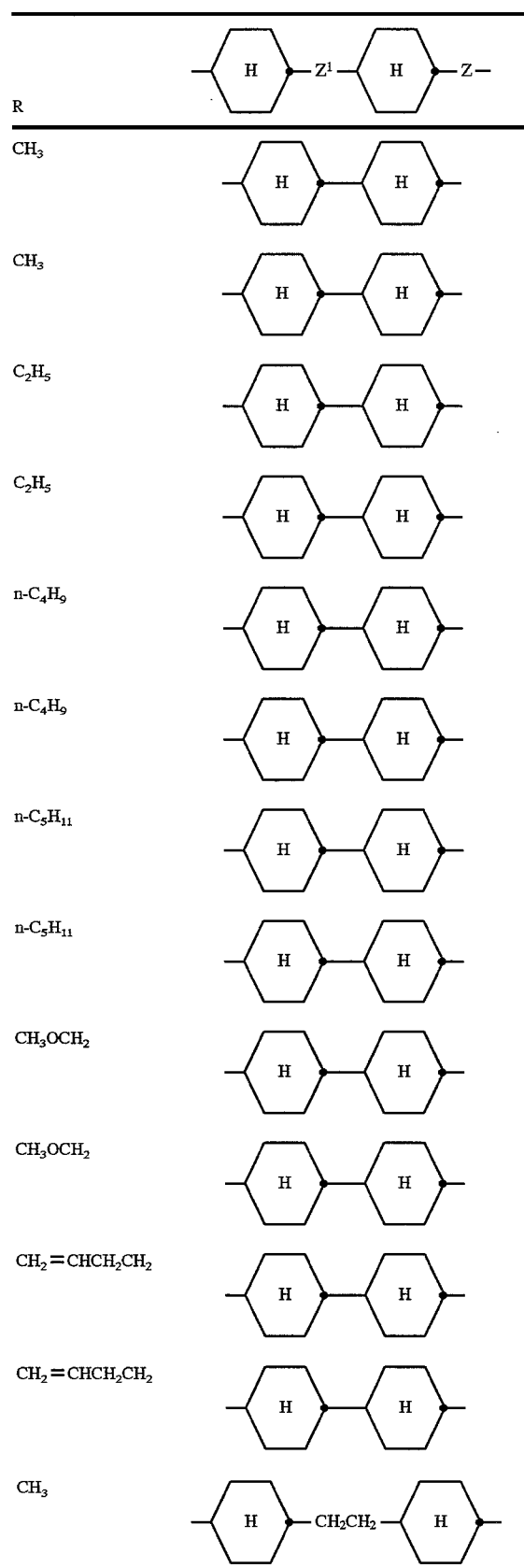
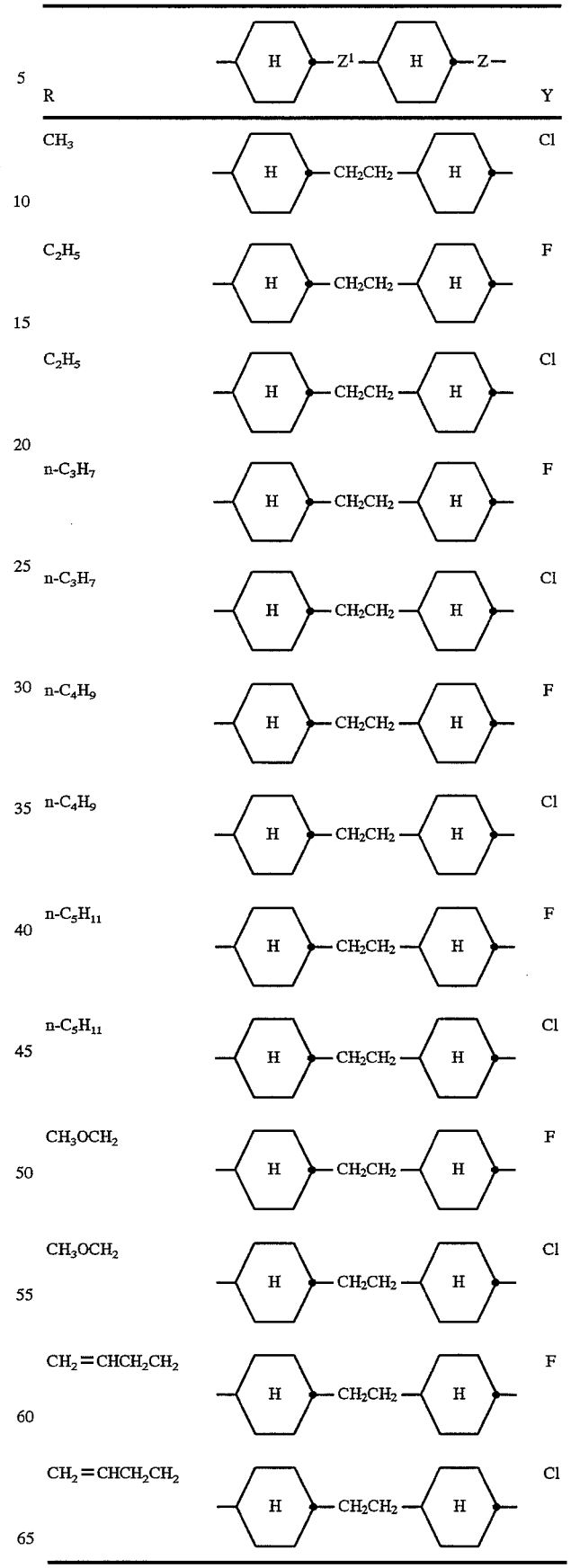

EXAMPLE 3 a) 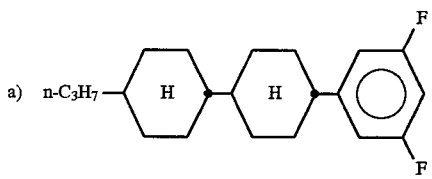

Two drops of bromine are added to a solution of 6.0 g of magnesium turnings in 60 ml of ether. A solution of 48.2 g of 3,5-difluorobromobenzene in 60 ml of ether is subsequently added dropwise. The mixture is stirred for a further 0.5 hour, and a solution of 44.5 g of 4-trans-(4-propylcyclohexyl)cyclohexanone in 50 ml of ether is then added dropwise to the Grignard reagent at 20°–25° C. The mixture is stirred for a further two hours, poured into 500 ml of water, acidified by means of 30 ml of conc. hydrochloric acid and extracted by shaking with ether. The organic phase is evaporated to give a residue and subsequently refluxed for 1 hour with 1,000 ml of toluene and 120 ml of 20% sulfuric acid.

After phase separation and neutralization by means of saturated sodium bicarbonate solution, the product is hydrogenated at 1 bar and 60° C. using 10 g of Pd/C (5%). The mixture is subsequently filtered and evaporated. Flash chromatography gives the pure product. C 60° N 87.6° I, $\Delta\epsilon=3.3$ b) 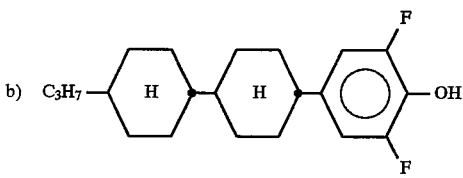

31 ml of n-BuLi (15% in hexane) are added dropwise at from −65° C. to −70° C. to a mixture of 47 mmol of 4-trans-(4-n-propylcyclohexyl)cyclohexyl-1-trans-(3,5-difluorobenzene), 50 mmol of TMEDA and 150 ml of THF, and the mixture is stirred at −70° C. for a further hour. Then, 57 mmol of trimethyl borate are added dropwise at from −85° to −90° C., followed by 65 mmol of acetic acid at −20° C.

c) 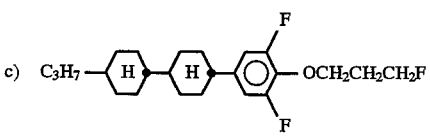

The difluorophenol is reacted analogously to Example 2 a) with 1-chloro-3-fluoropropane to give the phenol ether.

d) 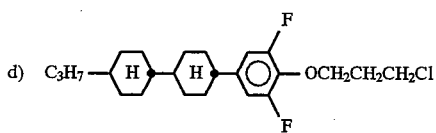

The difluorophenol prepared in Example 4b) is reacted analogously to Example 2b) with 1-chloro-3-iodopropane. C 50N 157.2 I, $\Delta\epsilon=5.7$.

EXAMPLE 4 a) 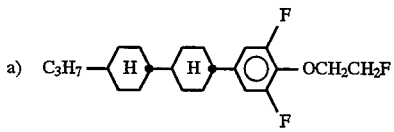

1 mmol of diethyl azodicarboxylate is added dropwise at 0°–10° C. to a solution comprising 1 mmol of 4-trans-(4-n-propylcyclohexyl)cyclohexyl-1-trans-(3,5-difluorophenol), 1 mmol of triphenylphosphine, 1 mmol of 2-fluoroethanol and 25 ml of THF. The mixture is subsequently stirred at room temperature for a further hour and then subjected to customary work-up. C 82N 165.5 I, $\Delta\epsilon=2.07$.

b) 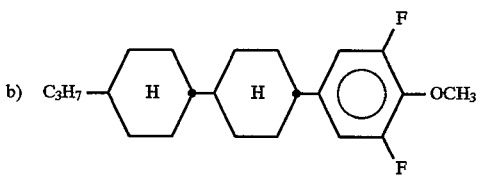

1 mmol of 4-trans-(4-n-propylcyclohexyl)cyclo-hexyl-1-trans-(3,5-difluorophenol) is reacted with methanol analogously to Example 4a). C 41N 151.8 I, $\Delta\epsilon=0.088$.

The following compounds of the formula

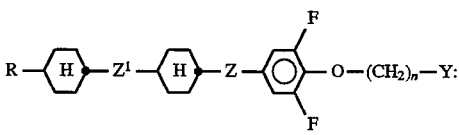

according to the invention are obtained analogously from the corresponding precursors:

| R | ⬡H—Z¹—⬡H—Z— | n | Y |
|---|---|---|---|
| CH₃ | 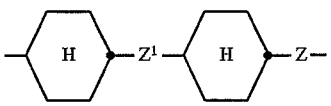 | 1 | H |
| CH₃ |  | 1 | F |
| CH₃ | 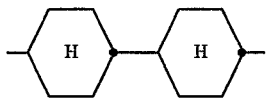 | 1 | Cl |
| CH₃ | 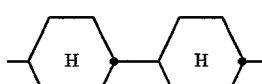 | 2 | F |
| CH₃ | 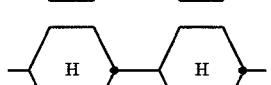 | 2 | Cl |
| CH₃ |  | 3 | F |
| CH₃ |  | 3 | Cl |
| CH₃ |  | 4 | F |
| CH₃ |  | 4 | Cl |
| CH₃ | 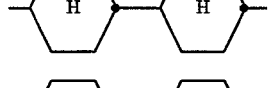 | 5 | F |
| CH₃ | 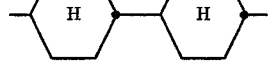 | 5 | Cl |
| C₂H₅ | 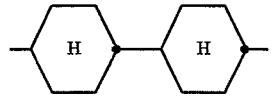 | 1 | F |
| C₂H₅ | 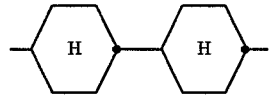 | 1 | Cl |
| C₂H₅ | 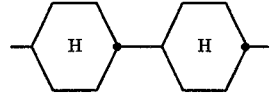 | 2 | F |

-continued

| R | ⬡H–Z¹–⬡H–Z– | n | Y |
|---|---|---|---|
| C₂H₅ | ⬡H–⬡H | 2 | Cl |
| C₂H₅ | ⬡H–⬡H | 3 | F |
| C₂H₅ | ⬡H–⬡H | 3 | Cl |
| C₂H₅ | ⬡H–⬡H | 4 | F |
| C₂H₅ | ⬡H–⬡H | 4 | Cl |
| C₂H₅ | ⬡H–⬡H | 5 | F |
| C₂H₅ | ⬡H–⬡H | 5 | Cl |
| n-C₃H₇ | ⬡H–⬡H | 1 | F |
| n-C₃H₇ | ⬡H–⬡H | 1 | Cl |
| n-C₃H₇ | ⬡H–⬡H | 2 | Cl |
| n-C₃H₇ | ⬡H–⬡H | 2 | F | K 82 N 165,5 I |
| n-C₃H₇ | ⬡H–⬡H | 3 | Cl |
| n-C₃H₇ | ⬡H–⬡H | 4 | F |
| n-C₃H₇ | ⬡H–⬡H | 4 | Cl |

-continued
| R | —⬡—Z¹—⬡—Z— | n | Y |
|---|---|---|---|
| n-C₃H₇ | 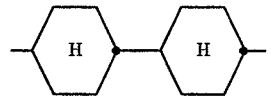 | 5 | F |
| n-C₃H₇ | 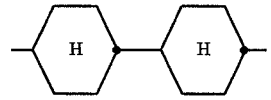 | 5 | Cl |
| n-C₄H₉ | 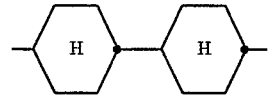 | 2 | F |
| n-C₄H₉ | 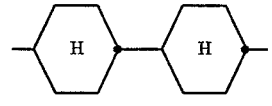 | 2 | Cl |
| n-C₄H₉ | 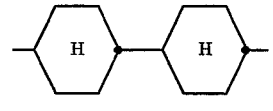 | 3 | F |
| n-C₄H₉ | 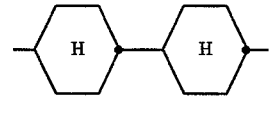 | 3 | Cl |
| n-C₅H₁₁ | 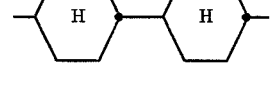 | 1 | H |
| n-C₅H₁₁ | 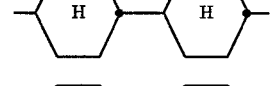 | 1 | F |
| n-C₅H₁₁ | 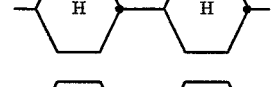 | 1 | Cl |
| n-C₅H₁₁ |  | 2 | F |
| n-C₅H₁₁ | 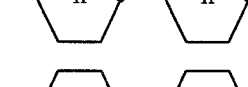 | 2 | Cl |
| n-C₅H₁₁ | 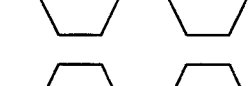 | 3 | F |
| n-C₅H₁₁ | 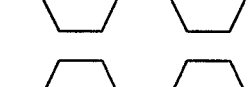 | 3 | Cl |
| n-C₅H₁₁ | 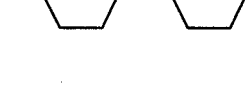 | 4 | F |

-continued

| R | ⟨H⟩–Z¹–⟨H⟩–Z– | n | Y |
|---|---|---|---|
| n-C₅H₁₁ | ⟨H⟩–⟨H⟩ | 4 | Cl |
| n-C₅H₁₁ | ⟨H⟩–⟨H⟩ | 5 | F |
| n-C₅H₁₁ | ⟨H⟩–⟨H⟩ | 5 | Cl |
| CH₃OCH₂ | ⟨H⟩–⟨H⟩ | 2 | F |
| CH₃OCH₂ | ⟨H⟩–⟨H⟩ | 2 | Cl |
| CH₃OCH₂ | ⟨H⟩–⟨H⟩ | 3 | F |
| CH₃OCH₂ | ⟨H⟩–⟨H⟩ | 3 | Cl |
| CH₂=CHCH₂CH₂ | ⟨H⟩–⟨H⟩ | 2 | F |
| CH₂=CHCH₂CH₂ | ⟨H⟩–⟨H⟩ | 2 | Cl |
| CH₂=CHCH₂CH₂ | ⟨H⟩–⟨H⟩ | 3 | F |
| CH₂=CHCH₂CH₂ | ⟨H⟩–⟨H⟩ | 3 | Cl |

EXAMPLE 5 a) 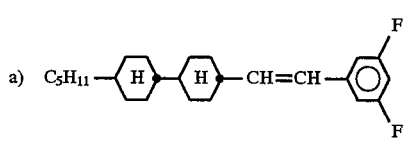

78 mmol of potassium tert.-butoxide, dissolved in 80 ml of THF, are added dropwise at −5° C. to 78 mmol of 1-(4-(4-n-pentylcyclohexyl)cyclohexyl) methylenetriphenyl-phosphonium iodide and 78 mmol of 3,5-difluorobenzaldehyde, dissolved in 50 ml of THF. The mixture is subsequently stirred at the same temperature for 15 minutes and at room temperature for a further 1.5 hours. The reaction mixture is hydrolyzed, neutralized by means of hydrochloric acid and subsequently subjected to customary work-up.

b) 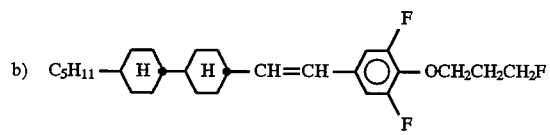

The product prepared in Example 5a) is reacted with 1-chloro-3-fluoropropane analogously to Example 3c) to give the phenol ether.

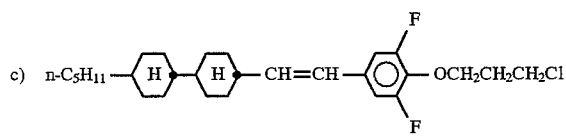

The product prepared in Example 5a) is reacted with 1-chloro-3-iodopropane analogously to Example 3d) to give the phenol ether.

The following compounds of the formula

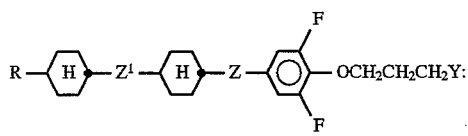

according to the invention are obtained analogously from the corresponding precursors of the formula II (L=F):

| R | —⟨H⟩—Z¹—⟨H⟩—Z— | Y |
|---|---|---|
| CH₃ | —⟨H⟩—⟨H⟩—CH=CH— | F |
| CH₃ | —⟨H⟩—⟨H⟩—CH=CH— | Cl |
| C₂H₅ | —⟨H⟩—⟨H⟩—CH=CH— | F |
| C₂H₅ | —⟨H⟩—⟨H⟩—CH=CH— | Cl |
| n-C₃H₇ | —⟨H⟩—⟨H⟩—CH=CH— | F |
| n-C₃H₇ | —⟨H⟩—⟨H⟩—CH=CH— | Cl |
| n-C₄H₉ | —⟨H⟩—⟨H⟩—CH=CH— | F |
| n-C₄H₉ | —⟨H⟩—⟨H⟩—CH=CH— | Cl |
| CH₃OCH₂ | —⟨H⟩—⟨H⟩—CH=CH— | F |
| CH₃OCH₂ | —⟨H⟩—⟨H⟩—CH=CH— | Cl |
| CH₂=CHCH₂CH₂ | —⟨H⟩—⟨H⟩—CH=CH— | F |
| CH₂=CHCH₂CH₂ | —⟨H⟩—⟨H⟩—CH=CH— | Cl |

EXAMPLE 6

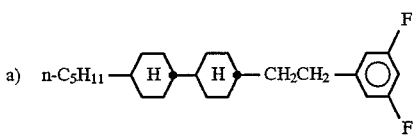

9 mmol of the product from Example 5a) are dissolved in 30 ml of THF, 0.3 g of 4% Pd-C is added, and the mixture is hydrogenated. The catalyst is subsequently filtered off, and the filtrate is evaporated in vacuo to give a residue. This is chromatographed on a silica gel column using pentane.

An analogous reaction gives

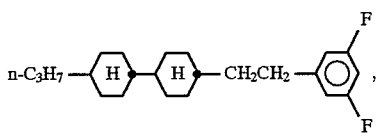

C 52 N 95.1 I, Δε = 4.7.

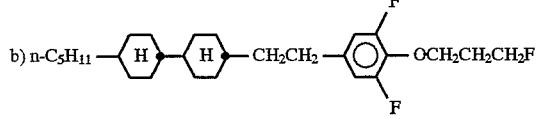

The product obtained in Example 6a) is reacted with 1-chloro-3-fluoropropane analogously to Example 3c).

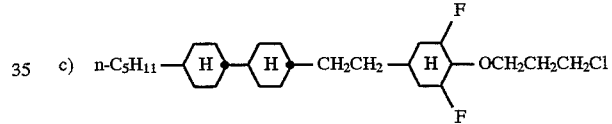

The product prepared in Example 6a) is reacted with 1-chloro-3-iodopropane analogously to Example 3d) to give the phenol ether.

The following compounds of the formula

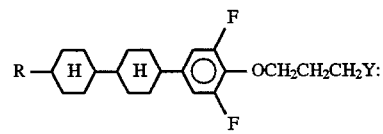

are obtained analogously from the corresponding precursors of the formula II (L=F):

| R | —⟨H⟩—Z¹—⟨H⟩—Z— | Y |
|---|---|---|
| CH₃ | —⟨H⟩—⟨H⟩—CH₂CH₂— | F |
| CH₃ | —⟨H⟩—⟨H⟩—CH₂CH₂— | Cl |

-continued

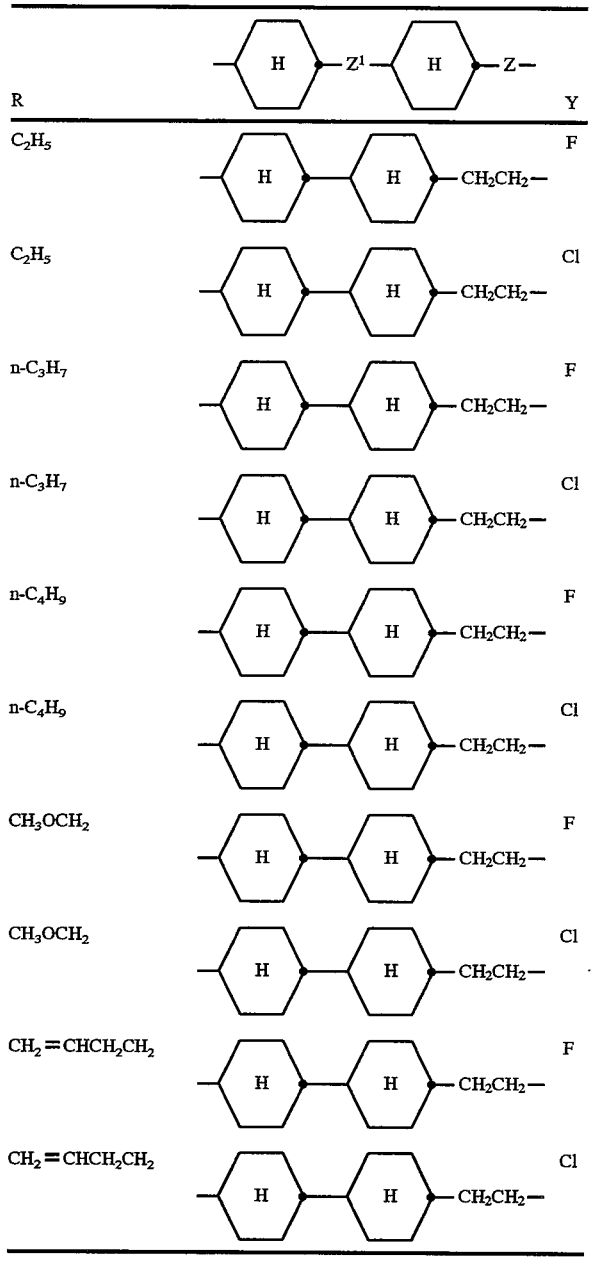

EXAMPLE 7

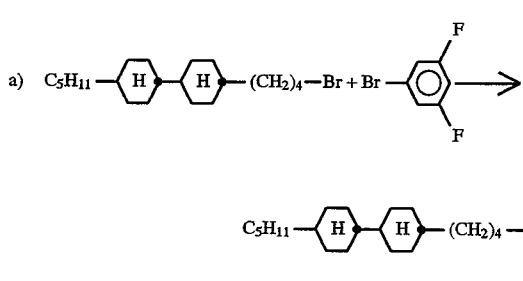

11.5 g of anhydrous zinc bromide and then 1.4 g of lithium granules are added to 0.1 mol of 4-(4-(n-pentylcyclohexyl)cyclohexylbutyl bromide in 150 ml of a solvent mixture comprising THF/toluene (1:4). The mixture is treated with ultrasound for 4 hours at between 0° C. and 10° C. under argon and with stirring. The organozinc compound produced is treated with 0.1 mol of 3,5-di-fluoro-1-dibromobenzene and 2 mol % of 1,1'-bis (diphenylphosphino)ferrocenepalladium(II) dichloride, the ultrasound bath and the cooling are removed, and the mixture is stirred at room temperature for 24 hours. 100 ml of saturated $NH_4C_1$ solution are added with stirring, the organic phase is separated off, and the aqueous phase is extracted with toluene. The combined organic extracts are dried, evaporated and chromatographed on silica gel.

b) 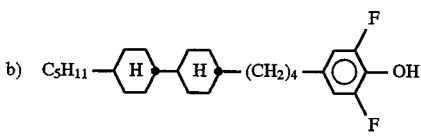

The reaction of the difluorobenzene with BuLi and trimethyl borate to give the difluorophenol is carried out analogously to Example 1.

c) 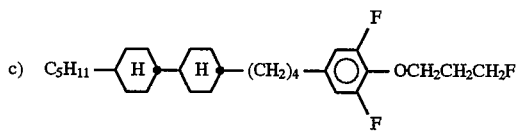

The difluorophenol from Example 7b) is reacted with 1-chloro-3-fluoropropane analogously to Example 3c) to give the phenol ether.

d) 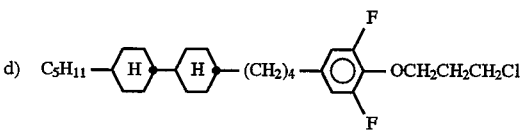

The product from Example 7b) is reacted with 1-chloro-3-iodopropane analogously to Example 3d).

The following compounds of the formula

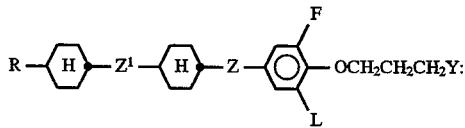

according to the invention are obtained analogously from the corresponding precursors of the formula II (L=H or F):

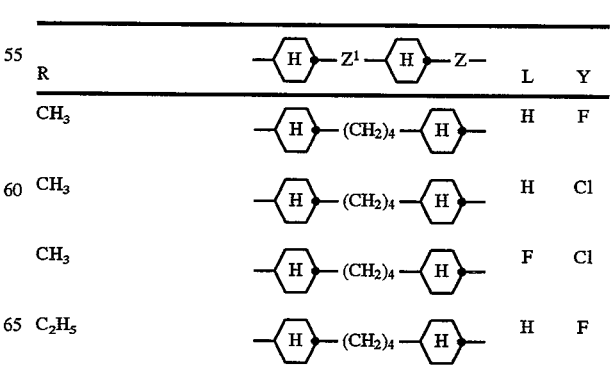

-continued

| R | -⟨H⟩-Z¹-⟨H⟩-Z- | L | Y |
|---|---|---|---|
| C₂H₅ | -⟨H⟩-(CH₂)₄-⟨H⟩- | F | F |
| n-C₃H₇ | -⟨H⟩-(CH₂)₄-⟨H⟩- | H | F |
| n-C₃H₇ | -⟨H⟩-(CH₂)₄-⟨H⟩- | H | Cl |
| n-C₃H₇ | -⟨H⟩-(CH₂)₄-⟨H⟩- | F | Cl |
| n-C₄H₉ | -⟨H⟩-(CH₂)₄-⟨H⟩- | F | F |
| n-C₄H₉ | -⟨H⟩-(CH₂)₄-⟨H⟩- | F | Cl |
| n-C₅H₁₁ | -⟨H⟩-(CH₂)₄-⟨H⟩- | H | F |
| n-C₅H₁₁ | -⟨H⟩-(CH₂)₄-⟨H⟩- | F | F |
| n-C₅H₁₁ | -⟨H⟩-(CH₂)₄-⟨H⟩- | F | Cl |
| CH₃OCH₂ | -⟨H⟩-(CH₂)₄-⟨H⟩- | H | F |
| CH₃OCH₂ | -⟨H⟩-(CH₂)₄-⟨H⟩- | F | F |
| CH₂=CHCH₂CH₂ | -⟨H⟩-(CH₂)₄-⟨H⟩- | H | F |
| CH₂=CHCH₂CH₂ | -⟨H⟩-(CH₂)₄-⟨H⟩- | F | F |
| CH₂=CHCH₂CH₂ | -⟨H⟩-(CH₂)₄-⟨H⟩- | F | Cl |

EXAMPLE 8

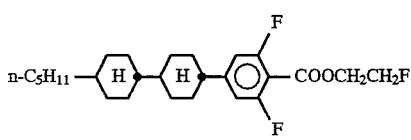

26 mm [sic] of 2-fluoroethanol and 0.1 g of DMAP are added to a suspension of 26 mmol of 4-trans-(4-pentylcyclohexyl)cyclohexyl-1-trans-3,5-difluorobenzoic acid (prepared as described in scheme 7) in 160 ml of dichloromethane. A solution of 6.6 g of DCC in 40 ml of dichloromethane is then added dropwise with stirring. The mixture is stirred overnight at room temperature. Oxalic acid is added, the mixture is stirred for a further hour, chromatographed using hexane and recrystallized. C 63 N 148.8 I The following compounds of the formula:

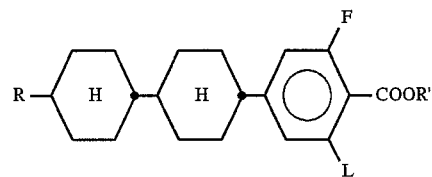

are obtained analogously:

| R | L | R' | |
|---|---|---|---|
| CH₃ | H | CH₂CH₂F | |
| C₂H₅ | H | CH₂CH₂F | |
| n-C₃H₇ | H | CH₂CH₂F | |
| n-C₄H₉ | H | CH₂CH₂F | |
| n-C₅H₁₁ | H | CH₂CH₂F | |
| CH₃OCH₂ | H | CH₂CH₂F | |
| CH₂=CHCH₂CH₂ | H | CH₂CH₂F | |
| CH₃ | F | CH₂CH₂F | |
| C₂H₅ | F | CH₂CH₂F | |
| n-C₃H₇ | F | CH₂CH₂F | |
| n-C₄H₉ | F | CH₂CH₂F | |
| CH₃OCH₂ | F | CH₂CH₂F | |
| CH₂=CHCH₂CH₂ | F | CH₂CH₂F | |
| CH₃ | F | CH₂CH₂Cl | |
| C₂H₅ | F | CH₂CH₂Cl | |
| n-C₃H₇ | F | CH₂CH₂Cl | |
| n-C₅H₁₁ | F | CH₂CH₂Cl | |
| CH₃OCH₂ | F | CH₂CH₂Cl | |
| CH₃ | F | CH₂CH₂CH₂Cl | |
| C₂H₅ | F | CH₂CH₂CH₂Cl | |
| n-C₃H₇ | F | CH₂CH₂CH₂Cl | |
| n-C₅H₁₁ | F | CH₂CH₂CH₂Cl | C 58 N 102 I |
| CH₃OCH₂ | F | CH₂CH₂CH₂Cl | |
| CH₂=CHCH₂CH₂ | F | CH₂CH₂CH₂Cl | |
| CH₃ | F | CH₂CH₂CH₂CF₃ | |
| C₂H₅ | F | CH₂CH₂CH₂CF₃ | |
| n-C₃H₇ | F | CH₂CH₂CH₂CF₃ | |
| n-C₅H₁₁ | F | CH₂CH₂CH₂CF₃ | C 65 N 86.9 I |
| CH₃OCH₂ | F | CH₂CH₂CH₂CF₃ | |
| CH₂=CHCH₂CH₂ | F | CH₂CH₂CH₂CF₃ | |
| CH₃ | F | CH₂CH₂OCF₃ | |
| C₂H₅ | F | CH₂CH₂OCF₃ | |
| n-C₃H₇ | F | CH₂CH₂OCF₃ | |
| n-C₅H₁₁ | F | CH₂CH₂OCF₃ | |
| CH₃OCH₂ | F | CH₂CH₂OCF₃ | |
| CH₂=CHCH₂CH₂ | F | CH₂CH₂OCF₃ | |
| CH₃ | F | CH₂CH₂CHF₂ | |
| C₂H₅ | F | CH₂CH₂CHF₂ | |
| n-C₃H₇ | F | CH₂CH₂CHF₂ | |
| n-C₅H₁₁ | F | CH₂CH₂CHF₂ | |
| CH₃OCH₂ | F | CH₂CH₂CHF₂ | |
| CH₂=CHCH₂CH₂ | F | CH₂CH₂CHF₂ | |

EXAMPLE 9

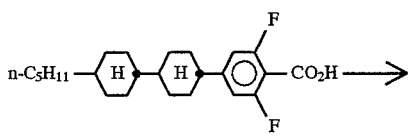

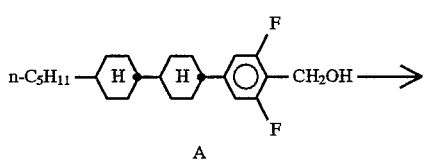

A

-continued

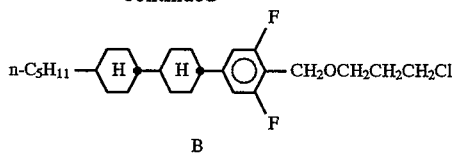

B

A suspension of 50 mmol of 4-trans-(4-pentyl-cyclohexyl)cyclohexyl-1-trans-3,5-(difluorobenzoic acid) in 150 ml of THF is added dropwise to a suspension of 50 mmol of lithium aluminum hydride in 50 ml of THF. The mixture is subsequently refluxed for a further 1 hour with stirring. The mixture is cooled in an ice bath and hydrolyzed by addition of 6 ml of 10% $NaHCO_3$ solution. 12 ml of 20% sodium hydroxide solution are added, and the organic phase is separated off, dried and evaporated.

A solution of 28 mmol of the difluorobenzyl alcohol A in 90 ml of THF is added to a solution of 30 mmol of sodium hydride in 30 ml of DMSO. 31 mmol of 3-chloro-1-iodopropane are then added, and the mixture is stirred over after [sic] at 50° C. Hydrolysis and conventional work-up give the ether B.

The following compounds of the formula

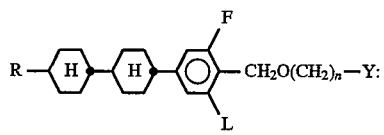

are obtained analogously:

| R | L | n | Y |
|---|---|---|---|
| $CH_3$ | H | 2 | F |
| $CH_3$ | F | 2 | F |
| $C_2H_5$ | H | 2 | Cl |
| $C_2H_5$ | H | 3 | Cl |
| $C_2H_5$ | F | 2 | Cl |
| $C_2H_5$ | F | 3 | Cl |
| $C_2H_5$ | H | 2 | F |
| $C_2H_5$ | H | 3 | F |
| $C_2H_5$ | F | 2 | F |
| $C_2H_5$ | F | 3 | F |
| $C_2H_5$ | H | 2 | $CF_3$ |

-continued

| R | L | n | Y |
|---|---|---|---|
| $C_2H_5$ | H | 3 | $CF_3$ |
| $C_2H_5$ | F | 2 | $CF_3$ |
| $C_2H_5$ | F | 3 | $CF_3$ |
| $n-C_3H_7$ | H | 2 | F |
| $n-C_3H_7$ | F | 2 | F |
| $n-C_3H_7$ | H | 2 | Cl |
| $n-C_3H_7$ | F | 2 | Cl |
| $n-C_3H_7$ | H | 2 | $OCF_3$ |
| $n-C_3H_7$ | F | 2 | $OCF_3$ |
| $n-C_3H_7$ | H | 2 | $CHF_2$ |
| $n-C_3H_7$ | F | 2 | $CHF_2$ |
| $n-C_3H_7$ | H | 2 | $CF_3$ |
| $n-C_3H_7$ | F | 2 | $CF_3$ |
| $n-C_5H_{11}$ | H | 2 | Cl |
| $n-C_5H_{11}$ | H | 2 | F |
| $n-C_5H_{11}$ | F | 2 | F |
| $n-C_5H_{11}$ | H | 2 | $CF_3$ |
| $n-C_5H_{11}$ | F | 2 | $CF_3$ |
| $n-C_5H_{11}$ | F | 3 | F |
| $n-C_5H_{11}$ | F | 3 | Cl |
| $n-C_5H_{11}$ | F | 3 | $CF_3$ |

EXAMPLE 10

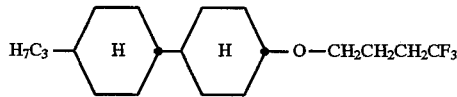

14.5 g (0.065 mol) of 4-(4-propylcyclohexyl)cyclohexanol are dissolved in 15 ml of THF, and 12.5 g (0.065 mol) of trifluorobutyl bromide, 1.2 g of cetyltrimethylammonium bromide, 5.2 g (0.13 mol) of sodium hydroxide solution and 0.3 ml of water are added successively. The mixture is stirred overnight at 70° C. The mixture is subsequently allowed to cool to room temperature and is taken up in diethyl ether. Conventional extractive work-up gives the ether, which is purified by chromatography on silica gel (hexane:ethyl acetate =9:1). C 10 $S_B$ 47 I.

The following trifluoroalkyl ethers of the formula

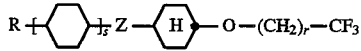

are prepared analogously:

| R | | $-O-(CH_2)_r-CF_3$ |
|---|---|---|
| $C_2H_5$ | (H)(H) | $OCH_2CH_2CF_3$ |
| $n-C_3H_7$ | (H)(H) | $OCH_2CH_2CF_3$ |
| $n-C_5H_{11}$ | (H)(H) | $OCH_2CH_2CF_3$ |

| R | —[⬡]₅—Z—⬡—H | —O—(CH₂)ᵣ—CF₃ |
|---|---|---|
| CH₃OCH₂ | —⬡(H)—⬡(H)— | OCH₂CH₂CF₃ |
| CH₂=CHCH₂CH₂ | —⬡(H)—⬡(H)— | OCH₂CH₂CF₃ |
| C₂H₅ | —⬡(H)—⬡(H)— | OCH₂CH₂CH₂CF₃ |
| n-C₄H₉ | —⬡(H)—⬡(H)— | OCH₂CH₂CH₂CF₃ |
| n-C₅H₁₁ | —⬡(H)—⬡(H)— | OCH₂CH₂CH₂CF₃ |
| CH₃OCH₂ | —⬡(H)—⬡(H)— | OCH₂CH₂CH₂CF₃ |
| CH₂=CHCH₂CH₂ | —⬡(H)—⬡(H)— | OCH₂CH₂CH₂CF₃ |
| C₂H₅ | —⬡(H)—⬡(H)— | OCH₂CH₂CH₂CH₂CF₃ |
| n-C₃H₇ | —⬡(H)—⬡(H)— | OCH₂CH₂CH₂CH₂CF₃ |
| n-C₅H₁₁ | —⬡(H)—⬡(H)— | OCH₂CH₂CH₂CH₂CF₃ |
| CH₃OCH₂ | —⬡(H)—⬡(H)— | OCH₂CH₂CH₂CH₂CF₃ |
| CH₂=CHCH₂CH₂ | —⬡(H)—⬡(H)— | OCH₂CH₂CH₂CH₂CF₃ |

EXAMPLE 11

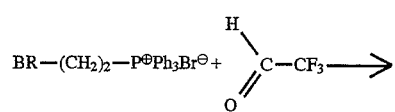

⟶

Br—CH₂—CH=CH—CF₃

11.5 g of potassium tert.-butoxide are added in portions at 0°–10° to a suspension of 0.1 mol of Wittig salt in 200 ml of THF. Trifluoroacetaldehyde gas is subsequently passed in at the same temperature until the orange ylide suspension has become colorless- The mixture is subsequently stirred at room temperature for 24 hours, poured into water, neutralized and extracted a number of times with toluene, and the toluene extract is dried, evaporated and filtered [sic] on silica gel using hexane.

The following trifluoroalkenyl ethers of the formula

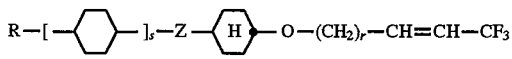

are prepared analogously:

| R | ⟨H⟩—Z—⟨H⟩ | —O—(CH$_2$)$_r$—CH=CH—CF$_3$ |
|---|---|---|
| C$_2$H$_5$ | ⟨H⟩—⟨H⟩ | OCH$_2$CH=CHCF$_3$ |
| n-C$_4$H$_9$ | ⟨H⟩—⟨H⟩ | OCH$_2$CH=CHCF$_3$ |
| n-C$_5$H$_{11}$ | ⟨H⟩—⟨H⟩ | OCH$_2$CH=CHCF$_3$ |
| CH$_3$OCH$_2$ | ⟨H⟩—⟨H⟩ | OCH$_2$CH=CHCF$_3$ |
| CH$_2$=CHCH$_2$CH$_2$ | ⟨H⟩—⟨H⟩ | OCH$_2$CH=CHCF$_3$ |
| C$_2$H$_5$ | ⟨H⟩—⟨H⟩ | OCH$_2$CH$_2$CH=CHCF$_3$ |
| n-C$_3$H$_7$ | ⟨H⟩—⟨H⟩ | OCH$_2$CH$_2$CH=CHCF$_3$ |
| n-C$_5$H$_{11}$ | ⟨H⟩—⟨H⟩ | OCH$_2$CH$_2$CH=CHCF$_3$ |
| CH$_3$OCH$_2$ | ⟨H⟩—⟨H⟩ | OCH$_2$CH$_2$CH=CHCF$_3$ |
| CH$_2$=CHCH$_2$CH$_2$ | ⟨H⟩—⟨H⟩ | OCH$_2$CH$_2$CH=CHCF$_3$ |

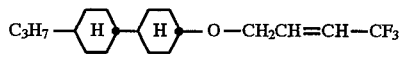

0.065 mol of 4-(4-propylcyclohexyl)cyclohexanol, 15 ml of THF, 0.065 mol of 1,1,1-trifluoro-4-bromobut-2-ene, 1.2 g of cetyltrimethylammonium bromide, 0.13 mol of sodium hydroxide solution and 0.3 ml of water are reacted analogously to Example 1.

EXAMPLE 12

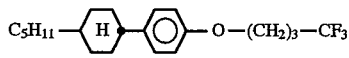

0.102 mol of diethyl azodicarboxylate is added dropwise with cooling to 0.1 mol of 4-(4-pentylcyclohexyl)phenol, 0.102 mol of triphenylphosphine and 0.1 mol of trifluorobutan-4-ol in 250 ml of tetrahydrofuran at room temperature. The mixture is subsequently stirred over-night.

The mixture is evaporated and the residue is filtered [sic] on silica gel using toluene.

The following trifluoroalkyl ethers of the formula

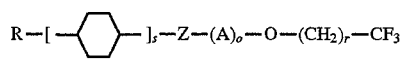

are prepared analogously:

| R | ⎯[○]$_s$⎯Z⎯(A)$_o$⎯ | ⎯O⎯(CH$_2$)$_r$⎯CF$_3$ |
|---|---|---|
| C$_2$H$_5$ | Cy(H)-Ph- | OCH$_2$CF$_3$ |
| n-C$_3$H$_7$ | Cy(H)-Ph- | OCH$_2$CF$_3$ |
| n-C$_5$H$_{11}$ | Cy(H)-Ph- | OCH$_2$CF$_3$ |
| CH$_3$OCH$_2$ | Cy(H)-Ph- | OCH$_2$CF$_3$ |
| CH$_2$=CHCH$_2$ | Cy(H)-Ph- | OCH$_2$CF$_3$ |
| C$_2$H$_5$ | Cy(H)-Ph- | OCH$_2$CH$_2$CF$_3$ |
| n-C$_3$H$_7$ | Cy(H)-Ph- | OCH$_2$CH$_2$CF$_3$ |
| n-C$_5$H$_{11}$ | Cy(H)-Ph- | OCH$_2$CH$_2$CF$_3$ |
| CH$_3$OCH$_2$ | Cy(H)-Ph- | OCH$_2$CH$_2$CF$_3$ |
| CH$_2$=CHCH$_2$ | Cy(H)-Ph- | OCH$_2$CH$_2$CF$_3$ |
| n-C$_3$H$_7$ | Cy(H)-Ph(F,F)- | OCH$_2$CH$_2$CF$_3$ |

| R | ⟨cyclohexane⟩-Z-(A)ₒ- | -O-(CH₂)ᵣ-CF₃ |
|---|---|---|
| n-C₅H₁₁ | 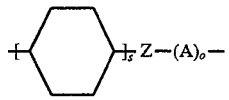 | OCH₂CH₂CF₃ |
| C₂H₅ | 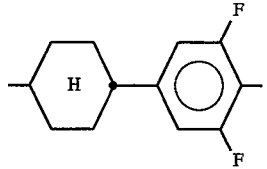 | OCH₂CH₂CH₂CF₃ |
| n-C₃H₇ | 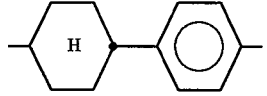 | OCH₂CH₂CH₂CF₃ |
| n-C₄H₉ | 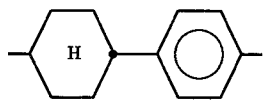 | OCH₂CH₂CH₂CF₃ |
| CH₃OCH₂ | 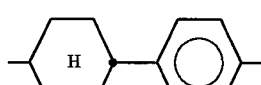 | OCH₂CH₂CH₂CF₃ |
| CH₂=CHCH₂ | 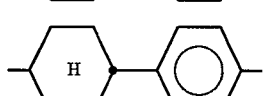 | OCH₂CH₂CH₂CF₃ |
| n-C₃H₇ | 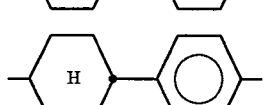 | OCH₂CH₂CH₂CF₃ |
| n-C₅H₁₁ | 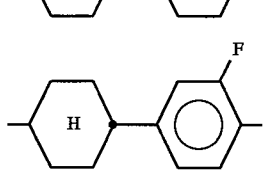 | OCH₂CH₂CH₂CF₃ |
| C₂H₅ | 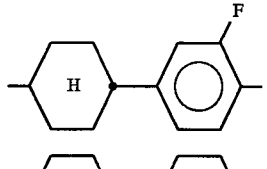 | OCH₂CH₂CH₂CH₂CF₃ |
| n-C₃H₇ | 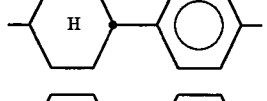 | OCH₂CH₂CH₂CH₂CF₃ |
| n-C₅H₁₁ | 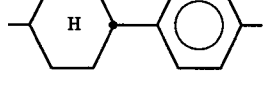 | OCH₂CH₂CH₂CH₂CF₃ |
| CH₃OCH₂ | 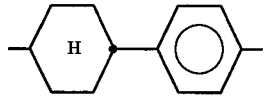 | OCH₂CH₂CH₂CH₂CF₃ |
| CH₂=CHCH₂ | 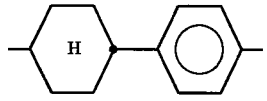 | OCH₂CH₂CH₂CH₂CF₃ |

-continued
| R | –[⬡]–Z–(A)$_o$– | –O–(CH$_2$)$_r$–CF$_3$ |
|---|---|---|
| n-C$_3$H$_7$ | 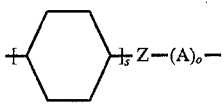 | OCH$_2$CH$_2$CH$_2$CH$_2$CF$_3$ |
| n-C$_5$H$_{11}$ | 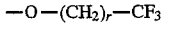 | OCH$_2$CH$_2$CH$_2$CH$_2$CF$_3$ |
| C$_2$H$_5$ | 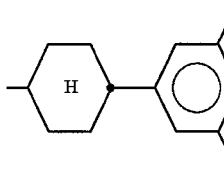 | OCH$_2$CF$_3$ |
| n-C$_3$H$_7$ | 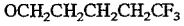 | OCH$_2$CF$_3$ |
| n-C$_5$H$_{11}$ | 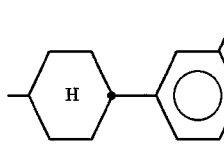 | OCH$_2$CF$_3$ |
| CH$_3$OCH$_2$ |  | OCH$_2$CF$_3$ |
| CH$_2$=CHCH$_2$CH$_2$ | 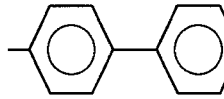 | OCH$_2$CF$_3$ |
| CH$_3$CH$_2$O |  | OCH$_2$CF$_3$ |
| CH$_3$CH$_2$CH$_2$CH$_2$O | 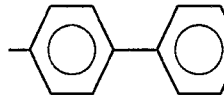 | OCH$_2$CF$_3$ |
| n-C$_3$H$_7$ | 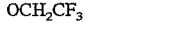 | OCH$_2$CF$_3$ |
| n-C$_5$H$_{11}$ | 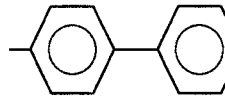 | OCH$_2$CF$_3$ |

-continued

| R |         ⟨cyclohexane⟩—Z—(A)$_o$— | —O—(CH$_2$)$_r$—CF$_3$ |
|---|---|---|
| C$_2$H$_5$ | 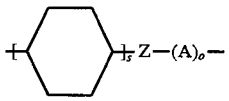 | OCH$_2$CH$_2$CF$_3$ |
| n-C$_3$H$_7$ | 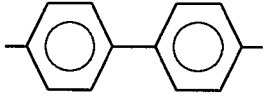 | OCH$_2$CH$_2$CF$_3$ |
| n-C$_5$H$_{11}$ | 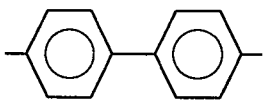 | OCH$_2$CH$_2$CF$_3$ |
| CH$_3$OCH$_2$ | 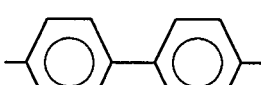 | OCH$_2$CH$_2$CF$_3$ |
| CH$_2$=CHCH$_2$CH$_2$ | 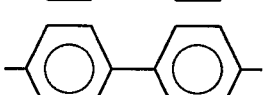 | OCH$_2$CH$_2$CF$_3$ |
| CH$_3$CH$_2$O | 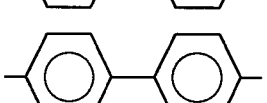 | OCH$_2$CH$_2$CF$_3$ |
| CH$_3$CH$_2$CH$_2$CH$_2$O |  | OCH$_2$CH$_2$CF$_3$ |
| n-C$_3$H$_7$ |  | OCH$_2$CH$_2$CF$_3$ |
| n-C$_5$H$_{11}$ | 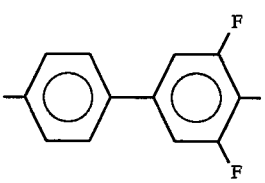 | OCH$_2$CH$_2$CF$_3$ |
| C$_2$H$_5$ | 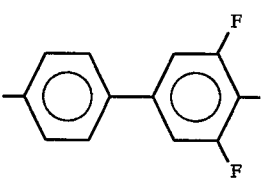 | OCH$_2$CH$_2$CH$_2$CF$_3$ |
| n-C$_3$H$_7$ | 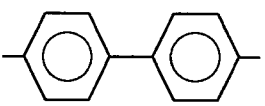 | OCH$_2$CH$_2$CH$_2$CF$_3$ |
| n-C$_5$H$_{11}$ | 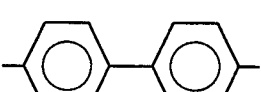 | OCH$_2$CH$_2$CH$_2$CF$_3$ |
| CH$_3$OCH$_2$ |  | OCH$_2$CH$_2$CH$_2$CF$_3$ |

-continued

| R | $+$⬡$+_s$Z—(A)$_o$— | —O—(CH$_2$)$_r$—CF$_3$ |
|---|---|---|
| CH$_2$=CHCH$_2$CH$_2$ | 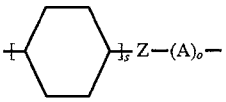 | OCH$_2$CH$_2$CH$_2$CF$_3$ |
| CH$_3$CH$_2$O | 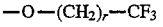 | OCH$_2$CH$_2$CH$_2$CF$_3$ |
| CH$_3$CH$_2$CH$_2$CH$_2$O | 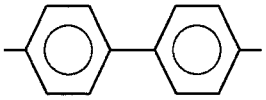 | OCH$_2$CH$_2$CH$_2$CF$_3$ |
| n-C$_3$H$_7$ | 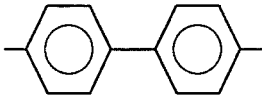 | OCH$_2$CH$_2$CH$_2$CF$_3$ |
| n-C$_5$H$_{11}$ | 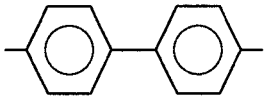 | OCH$_2$CH$_2$CH$_2$CF$_3$ |
| C$_2$H$_5$ | 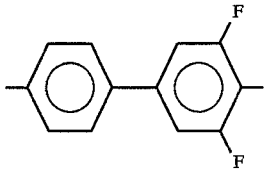 | OCH$_2$CH$_2$CH$_2$CH$_2$CF$_3$ |
| n-C$_3$H$_7$ | 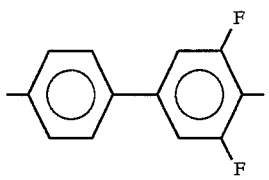 | OCH$_2$CH$_2$CH$_2$CH$_2$CF$_3$ |
| n-C$_5$H$_{11}$ | 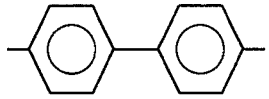 | OCH$_2$CH$_2$CH$_2$CH$_2$CF$_3$ |
| CH$_3$OCH$_2$ | 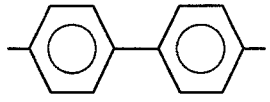 | OCH$_2$CH$_2$CH$_2$CH$_2$CF$_3$ |
| CH$_2$=CHCH$_2$CH$_2$ | 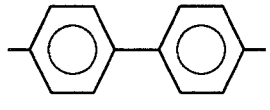 | OCH$_2$CH$_2$CH$_2$CH$_2$CF$_3$ |
| CH$_3$CH$_2$O | 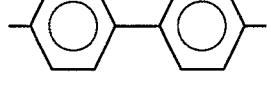 | OCH$_2$CH$_2$CH$_2$CH$_2$CF$_3$ |
| CH$_3$CH$_2$CH$_2$CH$_2$O | 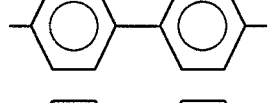 | OCH$_2$CH$_2$CH$_2$CH$_2$CF$_3$ |

-continued

| R | ⊢(cyclohexane)ₛ-Z-(A)ₒ- | -O-(CH₂)ᵣ-CF₃ |
|---|---|---|
| n-C₃H₇ | phenyl–phenyl(3,5-diF) | OCH₂CH₂CH₂CH₂CF₃ |
| n-C₅H₁₁ | phenyl–phenyl(3,5-diF) | OCH₂CH₂CH₂CH₂CF₃ |
| C₂H₅ | cyclohexane(H)–phenyl–phenyl | OCH₂CF₃ |
| n-C₃H₇ | cyclohexane(H)–phenyl–phenyl | OCH₂CF₃ |
| n-C₅H₁₁ | cyclohexane(H)–phenyl–phenyl | OCH₂CF₃ |
| CH₃OCH₂ | cyclohexane(H)–phenyl–phenyl | OCH₂CF₃ |
| CH₂=CHCH₂CH₂ | cyclohexane(H)–phenyl–phenyl | OCH₂CF₃ |
| C₂H₅ | cyclohexane(H)–phenyl–phenyl | OCH₂CH₂CF₃ |
| n-C₃H₇ | cyclohexane(H)–phenyl–phenyl | OCH₂CH₂CF₃ |
| n-C₅H₁₁ | cyclohexane(H)–phenyl–phenyl | OCH₂CH₂CF₃ |
| CH₃OCH₂ | cyclohexane(H)–phenyl–phenyl | OCH₂CH₂CF₃ |
| CH₂=CHCH₂CH₂ | cyclohexane(H)–phenyl–phenyl | OCH₂CH₂CF₃ |

-continued

| R | ![cyclohexane]-Z-(A)ₒ- | —O—(CH₂)ᵣ—CF₃ |
|---|---|---|
| n-C₃H₇ | Cy–Ph–Ph(3-F, 5-F)– | OCH₂CH₂CF₃ |
| CH₂=CHCH₂ | Cy–Ph–Ph(3-F, 5-F)– | OCH₂CH₂CF₃ |
| C₂H₅ | Cy–Ph–Ph– | OCH₂CH₂CH₂CF₃ |
| n-C₃H₇ | Cy–Ph–Ph– | OCH₂CH₂CH₂CF₃ |
| n-C₅H₁₁ | Cy–Ph–Ph– | OCH₂CH₂CH₂CF₃ |
| CH₃OCH₂ | Cy–Ph–Ph– | OCH₂CH₂CH₂CF₃ |
| CH₂=CHCH₂ | Cy–Ph–Ph– | OCH₂CH₂CH₂CF₃ |
| n-C₃H₇ | Cy–Ph–Ph(3-F, 5-F)– | OCH₂CH₂CH₂CF₃ |
| n-C₅H₁₁ | Cy–Ph–Ph(3-F, 5-F)– | OCH₂CH₂CH₂CF₃ |
| C₂H₅ | Cy–Ph–Ph– | OCH₂CH₂CH₂CH₂CF₃ |
| n-C₃H₇ | Cy–Ph–Ph– | OCH₂CH₂CH₂CH₂CF₃ |

-continued

| R | ⊢[⎔]<sub>s</sub>—Z—(A)<sub>o</sub>— | —O—(CH<sub>2</sub>)<sub>r</sub>—CF<sub>3</sub> |
|---|---|---|
| n-C<sub>5</sub>H<sub>11</sub> | 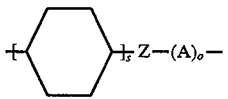 | OCH<sub>2</sub>CH<sub>2</sub>CH<sub>2</sub>CH<sub>2</sub>CF<sub>3</sub> |
| CH<sub>3</sub>OCH<sub>2</sub> | 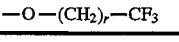 | OCH<sub>2</sub>CH<sub>2</sub>CH<sub>2</sub>CH<sub>2</sub>CF<sub>3</sub> |
| CH<sub>2</sub>=CHCH<sub>2</sub>CH<sub>2</sub> |  | OCH<sub>2</sub>CH<sub>2</sub>CH<sub>2</sub>CH<sub>2</sub>CF<sub>3</sub> |
| n-C<sub>3</sub>H<sub>7</sub> |  | OCH<sub>2</sub>CH<sub>2</sub>CH<sub>2</sub>CH<sub>2</sub>CF<sub>3</sub> |
| n-C<sub>3</sub>H<sub>7</sub> |  | OCH<sub>2</sub>CH<sub>2</sub>CH<sub>2</sub>CH<sub>2</sub>CF<sub>3</sub> |
| n-C<sub>5</sub>H<sub>11</sub> | 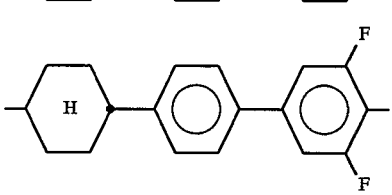 | OCH<sub>2</sub>CH<sub>2</sub>CH<sub>2</sub>CH<sub>2</sub>CF<sub>3</sub> |
| n-C<sub>5</sub>H<sub>11</sub> | 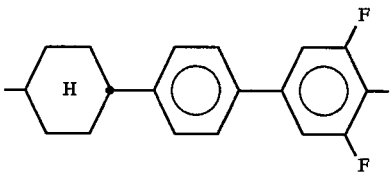 | OCH<sub>2</sub>CH<sub>2</sub>CH<sub>2</sub>CH<sub>2</sub>CF<sub>3</sub> |
| C<sub>2</sub>H<sub>5</sub> | 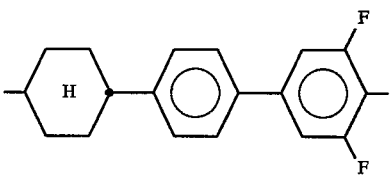 | OCH<sub>2</sub>CF<sub>3</sub> |
| n-C<sub>3</sub>H<sub>7</sub> |  | OCH<sub>2</sub>CF<sub>3</sub> |
| n-C<sub>5</sub>H<sub>11</sub> | 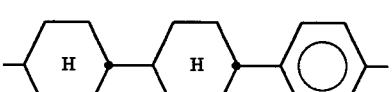 | OCH<sub>2</sub>CF<sub>3</sub> |
| CH<sub>3</sub>OCH<sub>2</sub> | 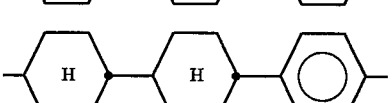 | OCH<sub>2</sub>CF<sub>3</sub> |
| CH<sub>2</sub>=CHCH<sub>2</sub>CH<sub>2</sub> | 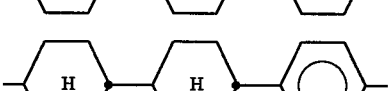 | OCH<sub>2</sub>CF<sub>3</sub> |

-continued
| R | -[cyclohexyl]-Z-(A)ₒ- | —O—(CH₂)ᵣ—CF₃ |
|---|---|---|
| n-C₃H₇ | 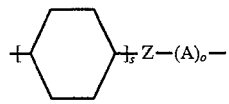 | OCH₂CF₃ |
| n-C₅H₁₁ | 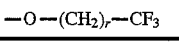 | OCH₂CF₃ |
| C₂H₅ | 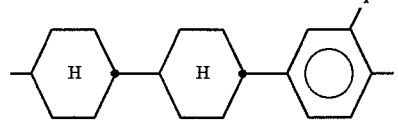 | OCH₂CH₂CF₃ |
| n-C₃H₇ | 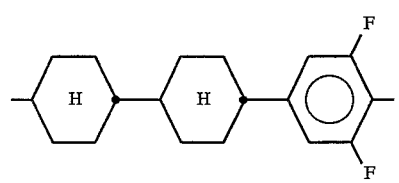 | OCH₂CH₂CF₃ |
| n-C₅H₁₁ | 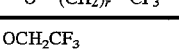 | OCH₂CH₂CF₃ |
| CH₃OCH₂ | 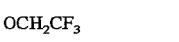 | OCH₂CH₂CF₃ |
| CH₂=CHCH₂CH₂ |  | OCH₂CH₂CF₃ |
| n-C₃H₇ | 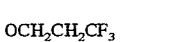 | OCH₂CH₂CF₃ |
| n-C₅H₁₁ | 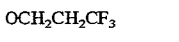 | OCH₂CH₂CF₃ |
| C₂H₅ | 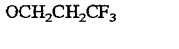 | OCH₂CH₂CH₂CF₃ |
| n-C₃H₇ |  | OCH₂CH₂CH₂CF₃ |
| n-C₅H₁₁ |  | OCH₂CH₂CH₂CF₃ |

-continued

| R | −[H]−Z−(A)ₒ− | −O−(CH₂)ᵣ−CF₃ |
|---|---|---|
| CH₃OCH₂ | −[H]−[H]−[Ph]− | OCH₂CH₂CH₂CF₃ |
| CH₂=CHCH₂ | −[H]−[H]−[Ph]− | OCH₂CH₂CH₂CF₃ |
| n-C₃H₇ | −[H]−[H]−[Ph(3,5-F₂)]− | OCH₂CH₂CH₂CF₃ |
| n-C₅H₁₁ | −[H]−[H]−[Ph(3,5-F₂)]− | OCH₂CH₂CH₂CF₃<br>C₆₁ S_B(56) N 145.2 I,<br>Δn = 0.096 |
| CH₃OCH₂ | −[H]−[H]−[Ph(3,5-F₂)]− | OCH₂CH₂CH₂CF₃ |
| n-C₃H₇ | −[H]−[H]−[Ph]− | OCH₂CH₂CH₂CH₂CF₃ |
| n-C₅H₁₁ | −[H]−[H]−[Ph]− | OCH₂CH₂CH₂CH₂CF₃ |
| CH₃OCH₂ | −[H]−[H]−[Ph]− | OCH₂CH₂CH₂CH₂CF₃ |
| CH₂=CHCH₂ | −[H]−[H]−[Ph]− | OCH₂CH₂CH₂CH₂CF₃ |
| n-C₃H₇ | −[H]−[H]−[Ph(3-F)]− | OCH₂CH₂CH₂CH₂CF₃ |
| C₂H₅ | −[H]−[H]−CH₂CH₂−[Ph]− | OCH₂CF₃ |

-continued

| R | ⎡⟨H⟩-⟨H⟩-⎤₃ Z—(A)ₒ— | —O—(CH₂)ᵣ—CF₃ |
|---|---|---|
| n-C₃H₇ | —⟨H⟩—⟨H⟩—CH₂CH₂—⟨○⟩— | OCH₂CF₃ |
| n-C₅H₁₁ | —⟨H⟩—⟨H⟩—CH₂CH₂—⟨○⟩— | OCH₂CF₃ |
| CH₃OCH₂ | —⟨H⟩—⟨H⟩—CH₂CH₂—⟨○⟩— | OCH₂CF₃ |
| CH₂=CHCH₂ | —⟨H⟩—⟨H⟩—CH₂CH₂—⟨○⟩— | OCH₂CF₃ |
| C₂H₅ | —⟨H⟩—⟨H⟩—CH₂CH₂—⟨○(F,F)⟩— | OCH₂CF₃ |
| n-C₃H₇ | —⟨H⟩—⟨H⟩—CH₂CH₂—⟨○(F)⟩— | OCH₂CF₃ |
| n-C₃H₇ | —⟨H⟩—⟨H⟩—CH₂CH₂—⟨○(F,F)⟩— | OCH₂CF₃ |
| C₂H₅ | —⟨H⟩—⟨H⟩—CH₂CH₂—⟨○⟩— | OCH₂CH₂CF₃ |
| n-C₃H₇ | —⟨H⟩—⟨H⟩—CH₂CH₂—⟨○⟩— | OCH₂CH₂CF₃ |
| n-C₅H₁₁ | —⟨H⟩—⟨H⟩—CH₂CH₂—⟨○⟩— | OCH₂CH₂CF₃ |
| CH₃OCH₂ | —⟨H⟩—⟨H⟩—CH₂CH₂—⟨○⟩— | OCH₂CH₂CF₃ |
| CH₂=CHCH₂ | —⟨H⟩—⟨H⟩—CH₂CH₂—⟨○⟩— | OCH₂CH₂CF₃ |

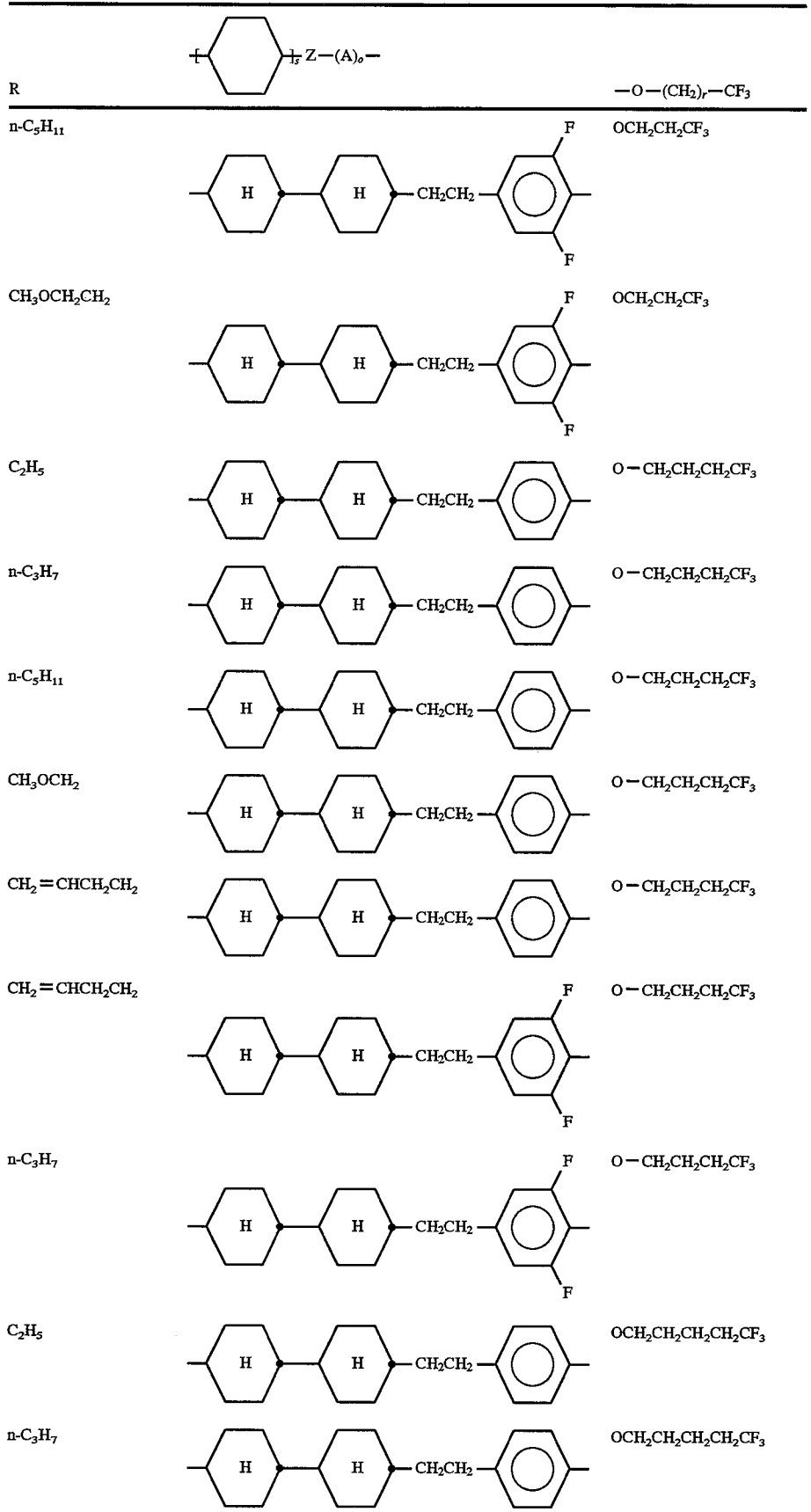

-continued

| R | ⊕─⟨H⟩─Z—(A)ₒ— | —O—(CH₂)ᵣ—CF₃ |
|---|---|---|
| n-C₅H₁₁ | —⟨H⟩—⟨H⟩—CH₂CH₂—⟨◯⟩— | OCH₂CH₂CH₂CH₂CF₃ |
| CH₃OCH₂ | —⟨H⟩—⟨H⟩—CH₂CH₂—⟨◯⟩— | OCH₂CH₂CH₂CH₂CF₃ |
| CH₂=CHCH₂ | —⟨H⟩—⟨H⟩—CH₂CH₂—⟨◯⟩— | OCH₂CH₂CH₂CH₂CF₃ |
| n-C₃H₇ | —⟨H⟩—⟨H⟩—CH₂CH₂—⟨◯⟩(F,F)— | OCH₂CH₂CH₂CH₂CF₃ |
| n-C₅H₁₁ | —⟨H⟩—⟨H⟩—CH₂CH₂—⟨◯⟩(F,F)— | OCH₂CH₂CH₂CH₂CF₃ |
| n-C₅H₁₁ | —⟨H⟩—⟨H⟩—CH₂CH₂—⟨◯⟩(F)— | OCH₂CH₂CH₂CH₂CF₃ |
| C₂H₅ | —⟨H⟩—(CH₂)₄—⟨◯⟩— | OCH₂CF₃ |
| n-C₃H₇ | —⟨H⟩—(CH₂)₄—⟨◯⟩— | OCH₂CF₃ |
| n-C₅H₁₁ | —⟨H⟩—(CH₂)₄—⟨◯⟩— | OCH₂CF₃ |
| CH₃OCH₂ | —⟨H⟩—(CH₂)₄—⟨◯⟩— | OCH₂CF₃ |
| CH₂=CHCH₂ | —⟨H⟩—(CH₂)₄—⟨◯⟩— | OCH₂CF₃ |
| n-C₃H₇ | —⟨H⟩—(CH₂)₄—⟨◯⟩(F,F)— | OCH₂CF₃ |

| R | ⊢〈 〉-Z—(A)ₒ— | —O—(CH₂)ᵣ—CF₃ |
|---|---|---|
| n-C₅H₁₁ | 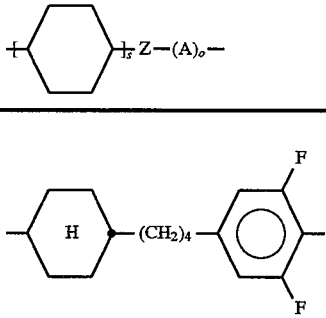 | OCH₂CF₃ |
| C₂H₅ | 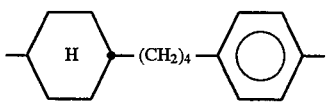 | OCH₂CH₂CF₃ |
| n-C₃H₇ | 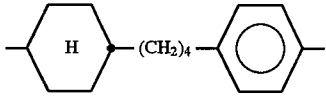 | OCH₂CH₂CF₃ |
| n-C₅H₁₁ | 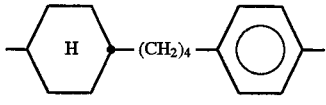 | OCH₂CH₂CF₃ |
| CH₃OCH₂ | 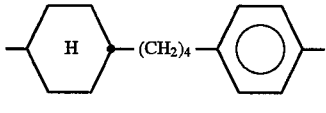 | OCH₂CH₂CF₃ |
| CH₂=CHCH₂ | 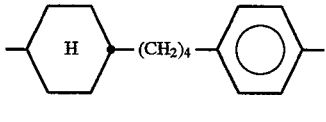 | OCH₂CH₂CF₃ |
| CH₃OCH₂CH₂ | 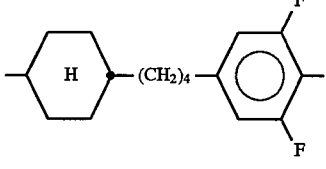 | OCH₂CH₂CF₃ |
| C₂H₅ | 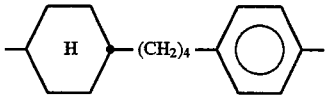 | OCH₂CH₂CH₂CF₃ |
| n-C₃H₇ | 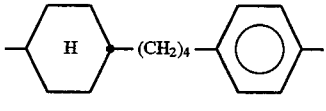 | OCH₂CH₂CH₂CF₃ |
| n-C₅H₁₁ | 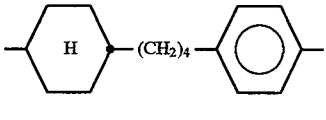 | OCH₂CH₂CH₂CF₃ |
| CH₃OCH₂ | 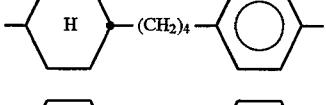 | OCH₂CH₂CH₂CF₃ |
| CH₂=CHCH₂ | 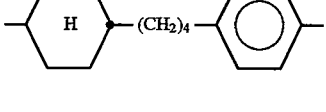 | OCH₂CH₂CH₂CF₃ |

-continued
| R | ⊢⟨ ⟩₅ Z—(A)ₒ— | —O—(CH₂)ᵣ—CF₃ |
|---|---|---|
| n-C₃H₇ | 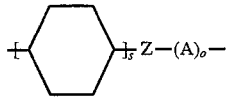 | OCH₂CH₂CH₂CF₃ |
| n-C₅H₁₁ | 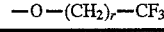 | OCH₂CH₂CH₂CF₃ |
| C₂H₅ | 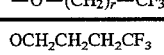 | OCH₂CH₂CH₂CH₂CF₃ |
| n-C₃H₇ | 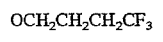 | OCH₂CH₂CH₂CH₂CF₃ |
| n-C₅H₁₁ | 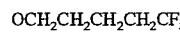 | OCH₂CH₂CH₂CH₂CF₃ |
| CH₃OCH₂ | 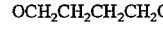 | OCH₂CH₂CH₂CH₂CF₃ |
| CH₂=CHCH₂CH₂ |  | OCH₂CH₂CH₂CH₂CF₃ |
| C₂H₅ |  | OCH₂CH₂CH₂CH₂CF₃ |
| n-C₃H₇ |  | OCH₂CH₂CH₂CH₂CF₃ |
| n-C₅H₁₁ |  | OCH₂CH₂CH₂CH₂CF₃ |

EXAMPLE 13

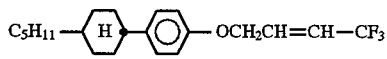

0.1 mol of 4-(4-pentylcyclohexyl)phenol and 0.1 mol of 1,1,1-trifluoro-4-bromobut-2-ene are reacted analogously to Example 3.

The following trifluoroalkenyl ethers of the formula

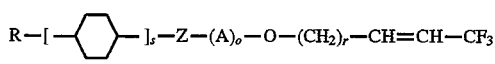

are prepared analogously.

| R | —[⬡]$_s$—Z—(A)$_o$— | —O—(CH$_2$)$_r$—CH=CH—CF$_3$ |
|---|---|---|
| C$_2$H$_5$ | Cy-Ph | OCH$_2$CH=CHCF$_3$ |
| n-C$_3$H$_7$ | Cy-Ph | OCH$_2$CH=CHCF$_3$ |
| n-C$_4$H$_9$ | Cy-Ph | OCH$_2$CH=CHCF$_3$ |
| CH$_3$OCH$_2$ | Cy-Ph | OCH$_2$CH=CHCF$_3$ |
| CH$_2$=CHCH$_2$CH$_2$ | Cy-Ph | OCH$_2$CH=CHCF$_3$ |
| C$_2$H$_5$ | Cy-Ph | OCH$_2$CH$_2$CH=CHCF$_3$ |
| n-C$_3$H$_7$ | Cy-Ph | OCH$_2$CH$_2$CH=CHCF$_3$ |
| n-C$_5$H$_{11}$ | Cy-Ph | OCH$_2$CH$_2$CH=CHCF$_3$ |
| CH$_3$OCH$_2$ | Cy-Ph | OCH$_2$CH$_2$CH=CHCF$_3$ |
| CH$_2$=CHCH$_2$CH$_2$ | Cy-Ph | OCH$_2$CH$_2$CH=CHCF$_3$ |
| n-C$_3$H$_7$ | Cy-Ph(F,F) | OCH$_2$CH$_2$CH=CHCF$_3$ |

-continued

| R | ⊢⟨⟩₅Z—(A)ₒ— | —O—(CH₂)ᵣ—CH=CH—CF₃ |
|---|---|---|
| n-C₅H₁₁ | 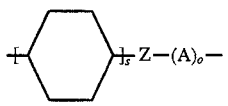 (Cy-H)—(Ph with F at 3,5) | OCH₂CH₂CH=CHCF₃ |
| C₂H₅ | 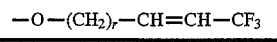 biphenyl | OCH₂CH=CHCF₃ |
| n-C₃H₇ | 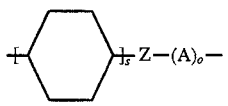 biphenyl | OCH₂CH=CHCF₃ |
| n-C₅H₁₁ | 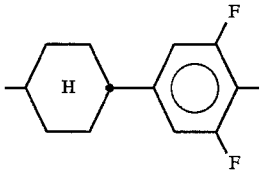 biphenyl | OCH₂CH=CHCF₃ |
| CH₃OCH₂ | 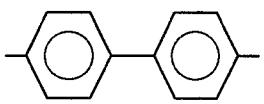 biphenyl | OCH₂CH=CHCF₃ |
| CH₂=CHCH₂ | 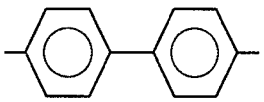 biphenyl | OCH₂CH=CHCF₃ |
| CH₃CH₂O | 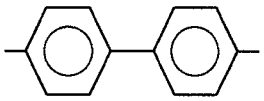 biphenyl | OCH₂CH=CHCF₃ |
| CH₃CH₂CH₂O | 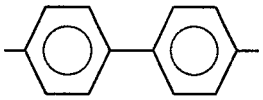 biphenyl | OCH₂CH=CHCF₃ |
| n-C₃H₇ | 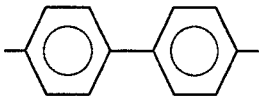 Ph—Ph(3,5-F₂) | OCH₂CH=CHCF₃ |
| n-C₅H₁₁ | 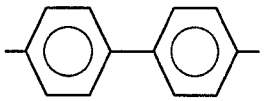 Ph—Ph(3,5-F₂) | OCH₂CH=CHCF₃ |
| C₂H₅ | 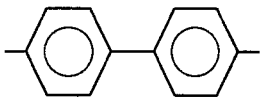 biphenyl | OCH₂CH₂CH=CHCF₃ |
| n-C₃H₇ | 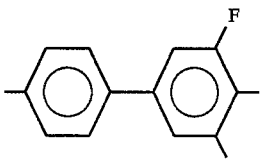 biphenyl | OCH₂CH₂CH=CHCF₃ |

-continued

| R | $+\!\!\left[\bigcirc\right]_{\!s}\!\!Z\!-\!(A)_o\!-$ | $-O-(CH_2)_r-CH=CH-CF_3$ |
|---|---|---|
| n-C$_5$H$_{11}$ | 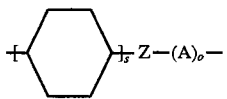 | OCH$_2$CH$_2$CH=CHCF$_3$ |
| CH$_3$OCH$_2$ | 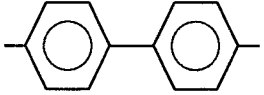 | OCH$_2$CH$_2$CH=CHCF$_3$ |
| CH$_2$=CHCH$_2$CH$_2$ | 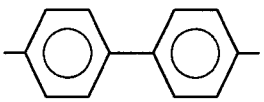 | OCH$_2$CH$_2$CH=CHCF$_3$ |
| CH$_3$CH$_2$O | 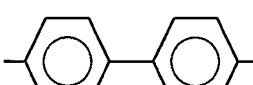 | OCH$_2$CH$_2$CH=CHCF$_3$ |
| CH$_3$CH$_2$CH$_2$CH$_2$O | 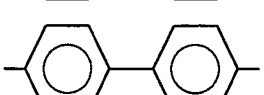 | OCH$_2$CH$_2$CH=CHCF$_3$ |
| C$_2$H$_5$ | 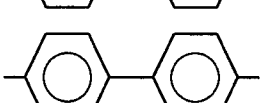 | OCH$_2$CH$_2$CH=CHCF$_3$ |
| n-C$_3$H$_7$ | 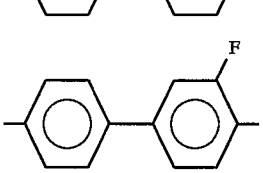 | OCH$_2$CH$_2$CH=CHCF$_3$ |
| n-C$_4$H$_9$ | 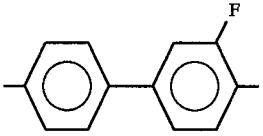 | OCH$_2$CH$_2$CH=CHCF$_3$ |
| CH$_3$OCH$_2$ | 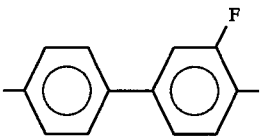 | OCH$_2$CH$_2$CH=CHCF$_3$ |
| CH$_2$=CHCH$_2$CH$_2$ | 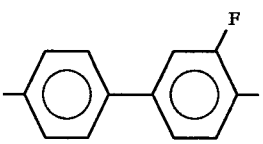 | OCH$_2$CH$_2$CH=CHCF$_3$ |
| CH$_2$=CHCH$_2$CH$_2$ | 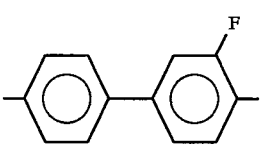 | OCH$_2$CH$_2$CH=CHCF$_3$ |
| C$_2$H$_5$ | 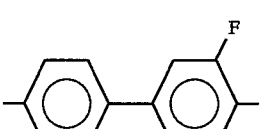 | OCH$_2$CH=CHCF$_3$ |

-continued
| R | ⊣〈H〉⊢Z—(A)ₒ— | —O—(CH₂)ᵣ—CH=CH—CF₃ |
|---|---|---|
| n-C₃H₇ | 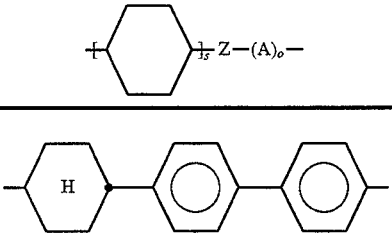 | OCH₂CH=CHCF₃ |
| n-C₅H₁₁ | 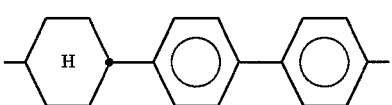 | OCH₂CH=CHCF₃ |
| CH₃OCH₂ | 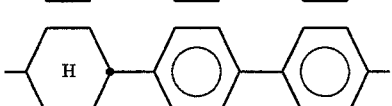 | OCH₂CH=CHCF₃ |
| CH₂=CHCH₂CH₂ | 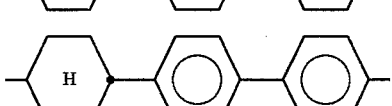 | OCH₂CH=CHCF₃ |
| n-C₃H₇ | 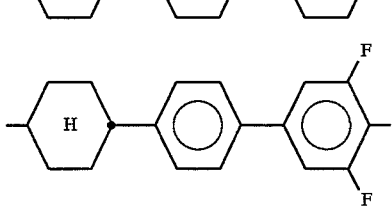 | OCH₂CH=CHCF₃ |
| n-C₅H₁₁ | 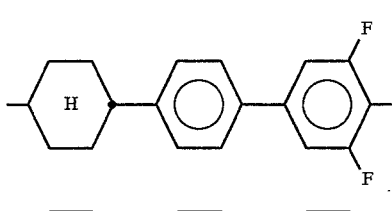 | OCH₂CH=CHCF₃ |
| C₂H₅ | 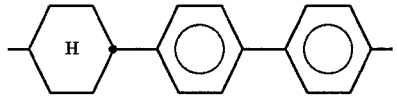 | OCH₂CH₂CH=CHCF₃ |
| n-C₃H₇ | 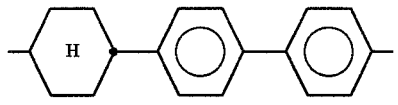 | OCH₂CH₂CH=CHCF₃ |
| n-C₅H₁₁ | 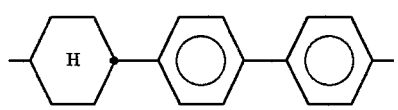 | OCH₂CH₂CH=CHCF₃ |
| CH₃OCH₂ | 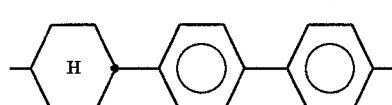 | OCH₂CH₂CH=CHCF₃ |
| CH₂=CHCH₂CH₂ | 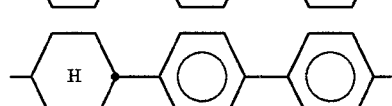 | OCH₂CH₂CH=CHCF₃ |
| n-C₅H₁₁ | 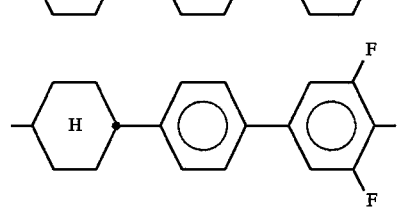 | OCH₂CH₂CH=CHCF₃ |

-continued

| R | ⊢⟨H⟩₅-Z-(A)ₒ- | -O-(CH₂)ᵣ-CH=CH-CF₃ |
|---|---|---|
| CH₃OCH₂CH₂ | -⟨H⟩-⟨○⟩-⟨○⟩- (F, F on last ring) | OCH₂CH₂CH=CHCF₃ |
| C₂H₅ | -⟨H⟩-⟨H⟩-⟨○⟩- | OCH₂CH=CHCF₃ |
| n-C₃H₇ | -⟨H⟩-⟨H⟩-⟨○⟩- | OCH₂CH=CHCF₃ |
| n-C₅H₁₁ | -⟨H⟩-⟨H⟩-⟨○⟩- | OCH₂CH=CHCF₃ |
| CH₃OCH₂ | -⟨H⟩-⟨H⟩-⟨○⟩- | OCH₂CH=CHCF₃ |
| CH₂=CHCH₂CH₂ | -⟨H⟩-⟨H⟩-⟨○⟩- | OCH₂CH=CHCF₃ |
| n-C₃H₇ | -⟨H⟩-⟨H⟩-⟨○⟩- (F, F) | OCH₂CH=CHCF₃ |
| n-C₅H₁₁ | -⟨H⟩-⟨H⟩-⟨○⟩- (F, F) | OCH₂CH=CHCF₃ |
| C₂H₅ | -⟨H⟩-⟨H⟩-⟨○⟩- | OCH₂CH₂CH=CHCF₃ |
| n-C₃H₇ | -⟨H⟩-⟨H⟩-⟨○⟩- | OCH₂CH₂CH=CHCF₃ |
| n-C₅H₁₁ | -⟨H⟩-⟨H⟩-⟨○⟩- | OCH₂CH₂CH=CHCF₃ |
| CH₃OCH₂ | -⟨H⟩-⟨H⟩-⟨○⟩- | OCH₂CH₂CH=CHCF₃ |

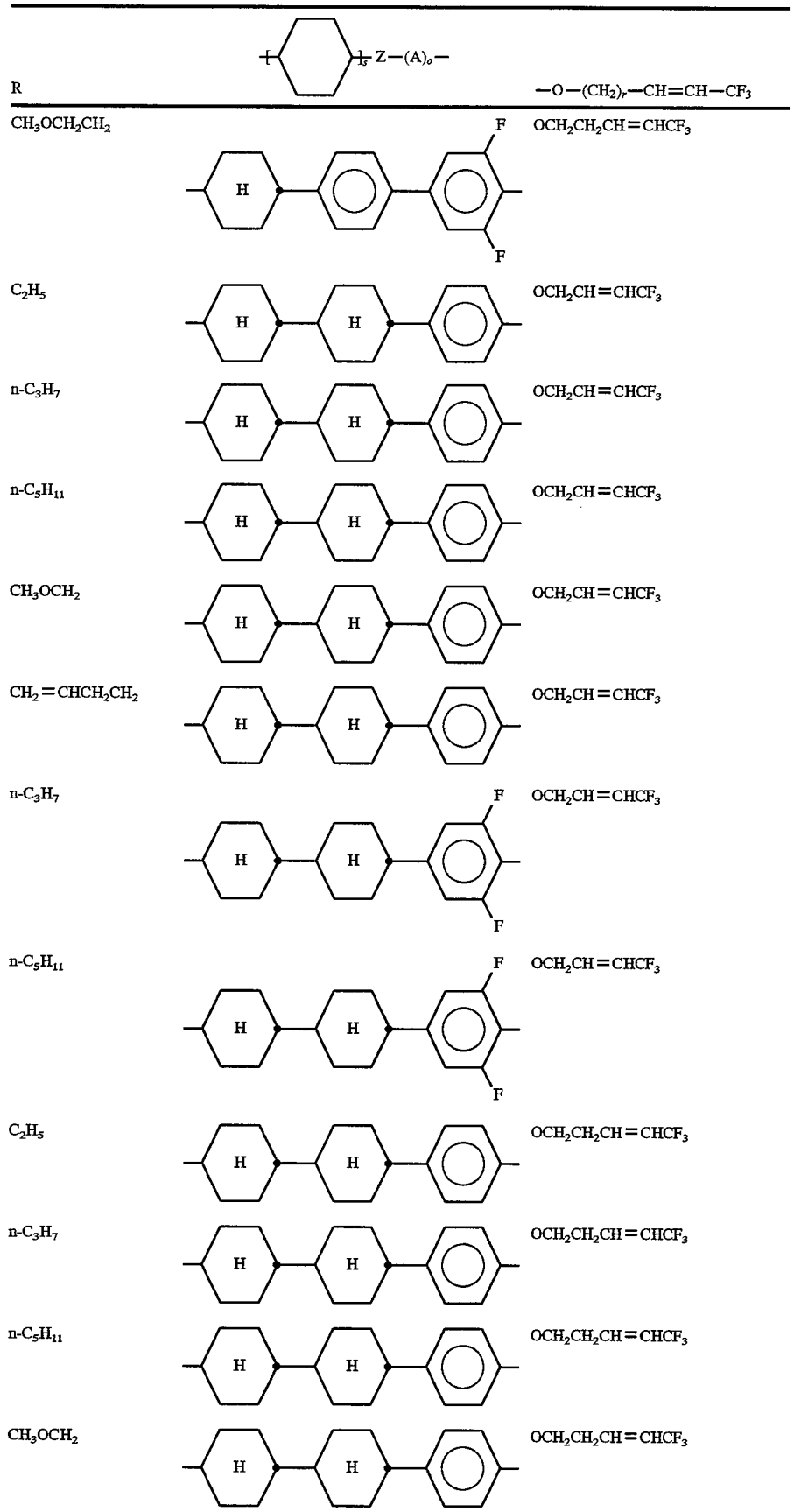

-continued
| R | —(H)₅—Z—(A)ₒ— | —O—(CH₂)ᵣ—CH=CH—CF₃ |
|---|---|---|
| CH₂=CHCH₂CH₂ | 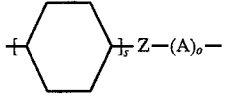 | OCH₂CH₂CH=CHCF₃ |
| n-C₃H₇ | 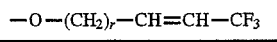 | OCH₂CH₂CH=CHCF₃ |
| n-C₅H₁₁ |  | OCH₂CH₂CH=CHCF₃ |
| CH₃OCH₂CH₂ | 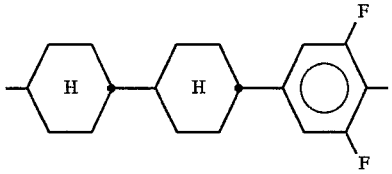 | OCH₂CH₂CH=CHCF₃ |
| C₂H₅ | 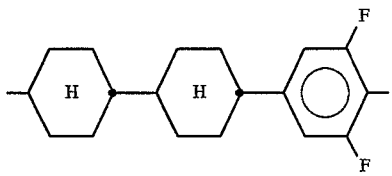 | OCH₂CH=CHCF₃ |
| n-C₃H₇ | 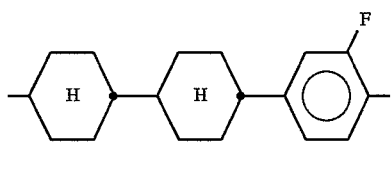 | OCH₂CH=CHCF₃ |
| n-C₅H₁₁ | 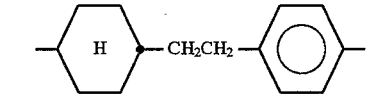 | OCH₂CH=CHCF₃ |
| CH₃OCH₂ | 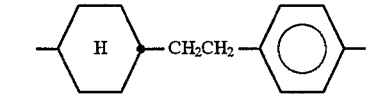 | OCH₂CH=CHCF₃ |
| CH₂=CHCH₂CH₂ | 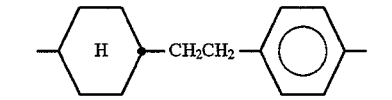 | OCH₂CH=CHCF₃ |
| C₂H₅ | 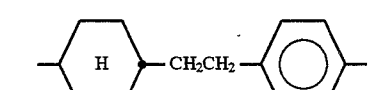 | OCH₂CH₂CH=CHCF₃ |
| n-C₃H₇ | 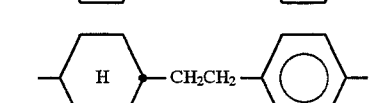 | OCH₂CH₂CH=CHCF₃ |
| n-C₅H₁₁ |  | OCH₂CH₂CH=CHCF₃ |

-continued

| R | ⊢⟨ H ⟩₅—Z—(A)ₒ— | —O—(CH₂)ᵣ—CH=CH—CF₃ |
|---|---|---|
| CH₃OCH₂ | 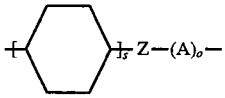 —⟨H⟩—CH₂CH₂—⟨○⟩— | OCH₂CH₂CH=CHCF₃ |
| CH₂=CHCH₂CH₂ | 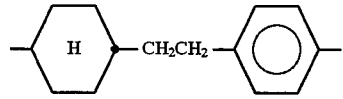 —⟨H⟩—CH₂CH₂—⟨○⟩— | OCH₂CH₂CH=CHCF₃ |
| C₂H₅ | 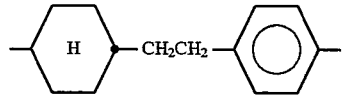 —⟨H⟩—(CH₂)₄—⟨○⟩— | OCH₂CH=CHCF₃ |
| n-C₃H₇ | 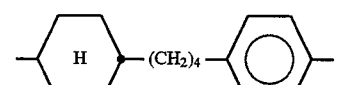 —⟨H⟩—(CH₂)₄—⟨○⟩— | OCH₂CH=CHCF₃ |
| n-C₅H₁₁ | 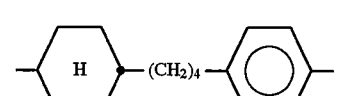 —⟨H⟩—(CH₂)₄—⟨○⟩— | OCH₂CH=CHCF₃ |
| CH₃OCH₂ |  —⟨H⟩—(CH₂)₄—⟨○⟩— | OCH₂CH=CHCF₃ |
| CH₂=CHCH₂CH₂ |  —⟨H⟩—(CH₂)₄—⟨○⟩— | OCH₂CH=CHCF₃ |
| C₂H₅ |  —⟨H⟩—(CH₂)₄—⟨○⟩— | OCH₂CH₂CH=CHCF₃ |
| n-C₃H₇ | 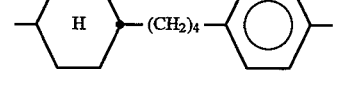 —⟨H⟩—(CH₂)₄—⟨○⟩— | OCH₂CH₂CH=CHCF₃ |
| n-C₅H₁₁ | 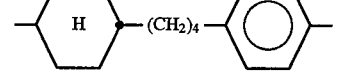 —⟨H⟩—(CH₂)₄—⟨○⟩— | OCH₂CH₂CH=CHCF₃ |
| CH₃OCH₂ | 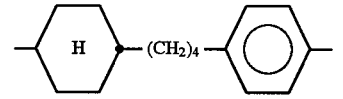 —⟨H⟩—(CH₂)₄—⟨○⟩— | OCH₂CH₂CH=CHCF₃ |
| CH₂=CHCH₂CH₂ | 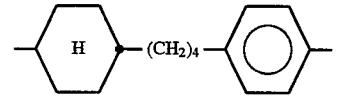 —⟨H⟩—(CH₂)₄—⟨○⟩— | OCH₂CH₂CH=CHCF₃ |
| C₂H₅ | 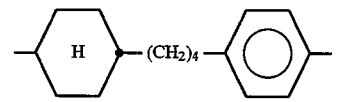 —⟨H⟩—(CH₂)₄—⟨○⟩(F)(F)— | OCH₂CH₂CH=CHCF₃ |

-continued

| R | ⟨H⟩—Z—(A)ₒ— | —O—(CH₂)ᵣ—CH=CH—CF₃ |
|---|---|---|
| n-C₃H₇ | 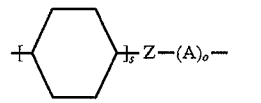 | OCH₂CH₂CH=CHCF₃ |
| n-C₅H₁₁ | 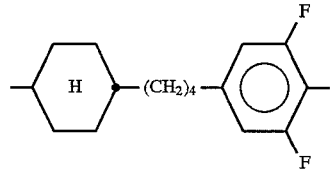 | OCH₂CH₂CH=CHCF₃ |
| CH₃OCH₂ | 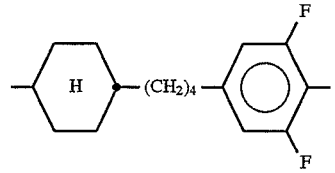 | OCH₂CH₂CH=CHCF₃ |
| CH₂=CHCH₂CH₂ | 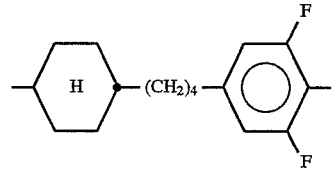 | OCH₂CH₂CH=CHCF₃ |

EXAMPLE 14

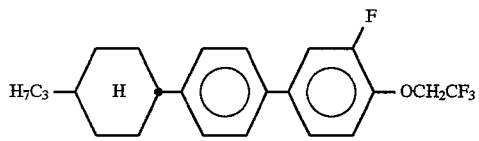

a) 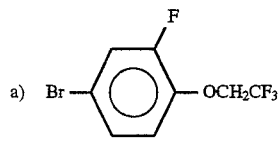

0.085 mol of 4-bromo-2-fluorophenolate [sic] are dissolved in 100 ml of 1,3-dimethyl-2-imidazolidinone, the solution is heated to 140° C. and 0.09 ml of 2,2,2-trifluoroethyl methylsulfonate is added dropwise. The solution is stirred at 140° C. for 24 hours. 500 ml of ice water are subsequently added, and the product is subjected to conventional work-up.

b) 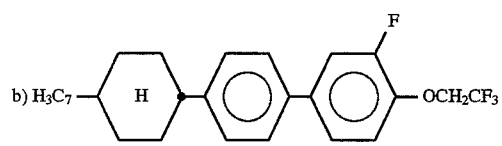

0.05 ml of trans-n-propylcyclohexylphenylboric acid, 20 ml of toluene, 10 ml of ethanol, 0.030 mol of sodium carbonate and 0.86 mmol of tetrakis(triphenylphosphine)palladium(O) [sic] are added to 0.015 mol of 4-bromo-2-fluorophenol 2,2,2-trifluoroethyl ether, and the mixture is refluxed for 2 hours. 100 ml of petroleum ether (40°–80°) are added, and the product is subjected to conventional work-up. C 81 S_B 101 S_A 133N 139.6 I. Δn=0.152.

The following compounds of the formula

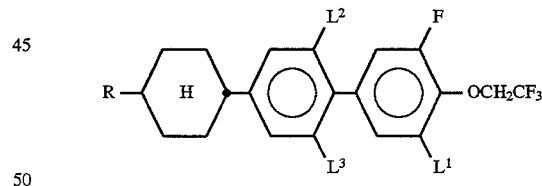

are prepared analogously:

| R | L¹ | L² | L³ | |
|---|---|---|---|---|
| C₂H₅ | H | H | H | |
| C₂H₅ | F | H | H | |
| C₂H₅ | F | F | F | C 96 I, Δn = 0.105 |
| n-C₃H₇ | F | H | H | C 83 N 104.6 I, Δn = 0.152 |
| n-C₃H₇ | F | F | F | C 98 I, Δn = 0.111 |
| n-C₅H₁₁ | H | H | H | |
| n-C₅H₁₁ | F | H | H | |
| n-C₅H₁₁ | F | F | F | |
| CH₃OCH₂ | H | H | H | |
| CH₃OCH₂ | F | H | H | |
| CH₃OCH₂ | F | F | F | |
| CH₂=CHCH₂CH₂ | F | F | F | |

EXAMPLE 15

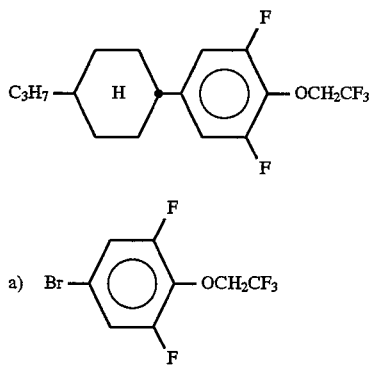

a) 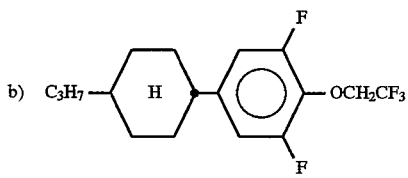

2,2,2-Trifluoroethyl methylsulfonate is added dropwise at 140° C. to 0.085 mol of 4-bromo-2,6-difluorophenolate [sic] analogously to Example 14a).

b) 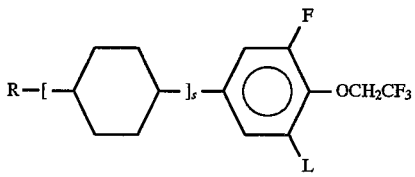

1.2 g of zinc chloride and 0.14 g of lithium granules are added to 0.01 mol of trans-4-n-propylcyclohexyl bromide in 15 ml of a solvent mixture comprising THF and toluene (1:4). The mixture is treated with ultrasound for 4 hours at between 0° and 10° C. under a protective gas and with stirring. The organozinc compound obtained is treated with 0.01 mol of 4-bromo-2,6-difluorophenol 2,2,2-trifluoroethyl ether and 2 mol % of 1,1'-bis(diphenylphosphino)ferrocenepalladium(II) dichloride, the ultrasound bath and the cooling are removed, and the mixture is stirred at room temperature for 24 hours. 10 ml of saturated ammonium chloride solution are added, and the organic phase is separated off and subjected to customary work-up. C 5 I, $\Delta n=0.038$.

The following compounds of the formula

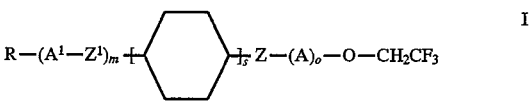

are prepared analogously:

| R | s | L | |
|---|---|---|---|
| n-C$_2$H$_5$ | 1 | H | |
| n-C$_2$H$_5$ | 1 | F | |
| n-C$_2$H$_5$ | 2 | H | C 65 S$_B$ 91 N 149.9 I, $\Delta n = 0.093$ |
| n-C$_2$H$_5$ | 2 | F | C 65 N 100.2 I, $\Delta n = 0.059$ |
| n-C$_3$H$_7$ | 1 | H | |
| n-C$_3$H$_7$ | 1 | F | |
| n-C$_3$H$_7$ | 2 | H | |
| n-C$_3$H$_7$ | 2 | F | C 69 N 140 I, $\Delta n = 0.092$ |
| n-C$_5$H$_{11}$ | 1 | H | |
| n-C$_5$H$_{11}$ | 1 | F | |
| n-C$_5$H$_{11}$ | 2 | H | C 62 S$_B$ 92 N 151.7 I, $\Delta n = 0.097$ |

-continued

| R | s | L |
|---|---|---|
| n-C$_5$H$_{11}$ | 2 | F |
| CH$_3$OCH$_2$ | 1 | H |
| CH$_3$OCH$_2$ | 1 | F |
| CH$_3$OCH$_2$ | 2 | H |
| CH$_3$OCH$_2$ | 2 | F |
| CH$_2$=CHCH$_2$CH$_2$ | 1 | H |
| CH$_2$=CHCH$_2$CH$_2$ | 1 | F |
| CH$_2$=CHCH$_2$CH$_2$ | 2 | H |
| CH$_2$=CHCH$_2$CH$_2$ | 2 | F |

We claim:

1. A nematic liquid-crystalline medium having at least two liquid-crystalline components, characterized in that it contains at least one compound of formula I $$R-(A^1-Z^1)_m \!-\!\!\left\langle\ \ \right\rangle\!\!-\!\!Z-(A)_o-O-CH_2CF_3 \quad I$$

in which

R is H, a straight-chain C$_{1-15}$-alkyl or C$_2$-C$_{15}$-alkenyl, it also being possible to replace one or more CH$_2$ groups in these radicals, independently of one another, by —O—, —S—,

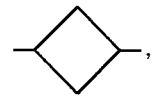

—CO—, —CO—O—, —O—CO— or —O—CO—O— in such a way that oxygen atoms are not linked directly to one another, Z$^1$ and Z are each, independently of one another, —CH$_2$CH$_2$—, —CH=CH—, —C≡C— or a single bond, and one of the radicals Z$^1$ and Z is optionally —(CH$_2$)$_4$— or —CH=CH—CH$_2$CH$_2$—, A and A$^1$ are each, independently of one another, trans-1,4-cyclohexylene in which, in addition, one or two non-adjacent CH$_2$ groups may be replaced by —O—, or are 1,4-phenylene which is unsubstituted or monosubstituted or disubstituted by fluorine and/or Cl atoms and in which, in addition, one or two CH groups may be replaced by N, m is 0, 1, 2 or 3, o and s are 0, 1 or 2, where (s+o) is $\geq 2$.

2. A medium according to claim 1 in which at least one group

A is 1,4-phenylene disubstituted by fluorine.

3. A medium according to claim 2 in which at least one group

A is

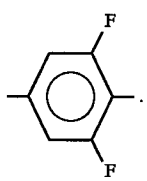

4. A medium according to claim 1 comprising at least one compound of formula Ib

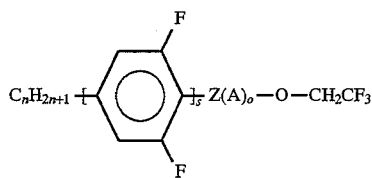

in which n is 1 to 7, s is 1 or 2, and A and Z are as defined in claim 1.

5. A medium according to claim 4 in which at least one group

A is 1,4-phenylene disubstituted by fluorine.

6. A medium according to claim 5 in which at least one group
A is

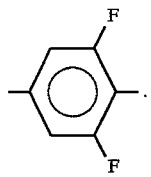

7. A medium according to claim 4 in which s=1 and A=1,4-phenylene.

8. Compounds of formula Ib as defined in claim 4 in which at least one group,

A is

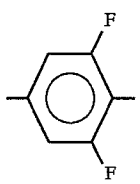

said compounds having nematic mesophases.

9. A nematic liquid crystalline medium having at least two liquid crystalline components, characterized in that it contains at least one compound of the formula

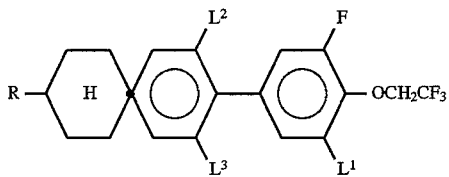

in which

R is H, a straight-chain alkyl or alkenyl radical having 1 to 15 carbon atoms, it also being possible to replace one or more $CH_2$ groups in these radicals, independently of one another, by —O—, —S—, — —, —CO—, —CO—O—, —O—CO— or —O—CO—O— in such a way that oxygen atoms are not linked directly to one another, and $L^1$, $L^2$ and $L^3$ are each, independently of one another, H or F.

* * * * *